(12) United States Patent
Mehrpour et al.

(10) Patent No.: US 10,287,298 B2
(45) Date of Patent: May 14, 2019

(54) NITROGEN-CONTAINING ANALOGS OF SALINOMYCIN, SYNTHESIS AND USE AGAINST CANCER STEM CELLS AND MALARIA

(71) Applicants: Centre National de la Recherche Scientifique (CNRS), Paris (FR); Institut National de la Sante et de la Recherche Medicale (INSERM), Paris (FR); Universite Paris Descartes, Paris (FR); Universtie Paris-SUD, Orsay (FR)

(72) Inventors: Maryam Mehrpour, L'hay les Roses (FR); Raphael Rodriguez, Vers-Pont-du-Gard (FR); Antje Hienzsch, Paris (FR); Mai Trang, Ho Chi Minh Ville (VN); Ahmed Hamai, Villetaneuse (FR)

(73) Assignees: Centre National de la Recherche Scientifique (CNRS), Paris (FR); Institut National de la Sante et de la Recherche Medicale (INSERM), Paris (FR); Universite Paris Descartes, Paris (FR)

( * ) Notice: Subject to any disclaimer, the term of this patent is extended or adjusted under 35 U.S.C. 154(b) by 0 days.

(21) Appl. No.: 15/510,427

(22) PCT Filed: Sep. 14, 2015

(86) PCT No.: PCT/EP2015/070975
§ 371 (c)(1),
(2) Date: Mar. 10, 2017

(87) PCT Pub. No.: WO2016/038223
PCT Pub. Date: Mar. 17, 2016

(65) Prior Publication Data
US 2017/0253610 A1    Sep. 7, 2017

(30) Foreign Application Priority Data
Sep. 12, 2014    (EP) .................................. 14306409

(51) Int. Cl.
C07H 7/06        (2006.01)
C07D 493/20      (2006.01)
A61K 31/337      (2006.01)
A61K 31/35       (2006.01)
A61K 31/366      (2006.01)
A61K 31/664      (2006.01)
A61K 31/704      (2006.01)
A61K 45/06       (2006.01)

(52) U.S. Cl.
CPC .......... C07D 493/20 (2013.01); A61K 31/337 (2013.01); A61K 31/35 (2013.01); A61K 31/366 (2013.01); A61K 31/664 (2013.01); A61K 31/704 (2013.01); A61K 45/06 (2013.01); C07H 7/06 (2013.01)

(58) Field of Classification Search
None
See application file for complete search history.

(56) References Cited

U.S. PATENT DOCUMENTS

2014/0371285 A1* 12/2014 Sprott .................. C07D 493/20
                                                       514/406

FOREIGN PATENT DOCUMENTS

WO    WO 2013/103993    7/2013

* cited by examiner

*Primary Examiner* — Traviss C McIntosh, III
(74) *Attorney, Agent, or Firm* — Buchanan Ingersoll & Rooney PC

(57) ABSTRACT

The present invention concerns compounds of formula (I), enantiomers, mixture of enantiomers, diastereoisomers and mixture of diastereoisomers thereof formula (I): wherein at least one of W, X and Y is selected from the group consisting of —$NR_1R_2$; —$NR_3$—$(CH_2)_n$—$NR_4R_5$; —O—$(CH_2)_n$—$NR_4R_5$; —$NR_3$—$(CH_2)_n$—$N'R_6R_7R_8$; and —O—$(CH_2)_n$—$N'R_6R_7R_8$ and Z is a functional group capable of chelating iron salts. The present invention also concerns the compounds of formula (I) for use as a drug, in particular, in the treatment of cancer and malaria.

(I)

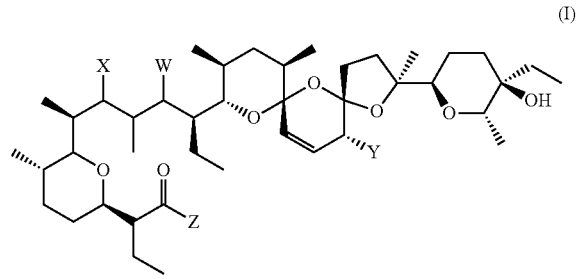

28 Claims, 18 Drawing Sheets

1A

1B

1C

1D

3A

3B

FACS analysis to monitor the extent of apoptosis as measured by annexin V positivity

NITROGEN-CONTAINING ANALOGS OF SALINOMYCIN, SYNTHESIS AND USE AGAINST CANCER STEM CELLS AND MALARIA

CROSS-REFERENCE TO RELATED APPLICATIONS

This application is a U.S. National Stage Application pursuant to 35 U.S.C. § 371 of International Patent Application PCT/EP2015/070975, filed on Sep. 14, 2015, and published as WO 2016/038223 on Mar. 17, 2016, which claims priority to European Patent Application 14306409.5, filed on Sep. 12, 2014, all of which are incorporated herein by reference in their entireties for all purposes.

FIELD OF THE INVENTION

The present invention concerns amino-derivatives of salinomycin, processes for their preparation and their use as a drug, in particular in the treatment of cancer and in the treatment of malaria.

STATE OF THE ART

Salinomycin is a monocarboxylic polyether possessing ionophoric properties of the following formula:

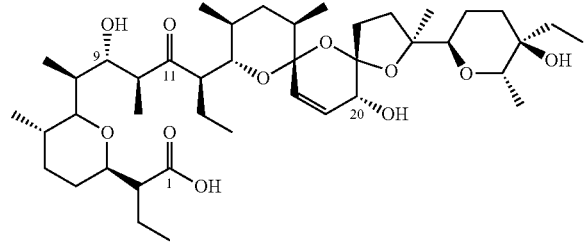

To date, salinomycin has been widely employed in veterinary medicine as an antibiotic and an anticoccidial.

Recently, the screening of 16000 compounds enabled identifying a small number of compounds capable of killing selectively cancer stem cells (CSCs) and tumor initiating cells (TICs), without affecting normal cells. This study demonstrated that targeting CSCs and TICs enabled the regression of the tumor mass and prevented metastasis.

In this study, salinomycin was identified as a potent compound against these cells, being capable of reducing the amount of TICs with a 100-fold higher efficacy than paclitaxel, a commonly employed anti-cancer drug.

Other studies have also shown that salinomycin induces cell death in chronic lymphocytic leukemia cells by inhibiting the Wnt path, in prostate cancer cells by inducing reactive oxygen species and by inducing a drop of mitochondrial membrane potential.

Salinomycin, however has the drawback of being neurotoxic, leading to peripheral neuropathies. In addition, its activity against CSCs and TICs remains moderate.

Analogs of salinomycin have been described in prior art. The modifications of salinomycin essentially consist in the replacement of the 1-carboxylic acid function by an ester, or the acylation of the 20-hydroxyl group of salinomycin.

There is therefore a need to improve the activity of salinomycine against CSCs and TICs, but also to design derivatives of this compound having reduced neurotoxicity.

The inventors of the present invention have discovered that 9- and/or 11- and/or 20-amino derivatives of salinomycine possess a superior activity against CSCs and TICs.

The ability of salinomycin to accumulate in lysosomes and to promote the formation of reactive oxygen species (ROS) and lysosomal membrane permeabilization is pointing toward the role of salinomycin derivatives in chelating iron to catalyze the Fenton reaction (that is the conversion of $H_2O_2$ into ROS mediated by iron complexes). Therefore, salinomycin derivative bearing chemical modifications that favor iron binding and the Fenton reaction are of considerable interest.

The present invention therefore concerns 9- and/or 11- and/or 20-amino derivatives of salinomycine, enantiomers, mixture of enantiomers, diastereoisomers and mixture of diasteroisomers thereof, of formula (I):

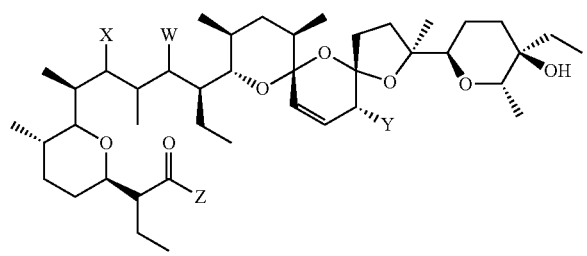

wherein:

W is selected from the group consisting of =O; $-NR_1R_2$; $-NR_3-(CH_2)_n-NR_4R_5$; $-O-(CH_2)_n-NR_4R_5$; $-NR_3-(CH_2)_n-N^+R_6R_7R_8$; and $-O-(CH_2)_n-N^+R_6R_7R_8$;

X is selected from the group consisting of =O, OH; $-NR_1R_2$; $-NR_3-(CH_2)_n-NR_4R_5$; $-O-(CH_2)_n-NR_4R_5$; $-NR_3-(CH_2)_n-N^+R_6R_7R_8$; and $-O-(CH_2)_n-N^+R_6R_7R_8$, Y is selected from the group consisting of OH; =N—OH; $-NR_1R_2$; $-NR_3-(CH_2)_n-NR_4R_5$; $-O-(CH_2)_n-NR_4R_5$; $-NR_3-(CH_2)_nN^+R_6R_7R_8$; and $-O-(CH_2)_n-N^+R_6R_7R_8$, $R_1$ and $R_2$, identical or different, are selected from the group consisting of H; $(C_1-C_{16})$-alkyl; $(C_3-C_{16})$-alkenyl; $(C_3-C_{16})$-alkynyl; $(C_3-C_{16})$-cycloalkyl; aryl; heteroaryl; $(C_1-C_6)$-alkyl-aryl; $(C_1-C_6)$-alkyl-heteroaryl; or $R_1$ represents H and $R_2$ represents $OR_9$, where $R_9$ is H, $(C_1-C_6)$-alkyl, aryl and $(C_1-C_6)$-alkyl-aryl;

$R_3$ is selected from the group consisting of H; $(C_1-C_6)$-alkyl; $(C_1-C_6)$-alkyl-aryl;

$R_4$ and $R_5$, identical or different, are selected from the group consisting of H; $(C_1-C_6)$-alkyl; aryl; $(C_1-C_6)$-alkylaryl;

$R_6$, $R_7$ and $R_8$, identical or different, are selected from the group consisting of $(C_1-C_6)$-alkyl; aryl; $(C_1-C_6)$-alkylaryl;

with the proviso that at least one of W, X and Y is selected from the group consisting of $-N^+R_1R_2$; $-NR_3-(CH_2)_n-NR_4R_5$; $-O-(CH_2)_n-NR_4R_5$; $-NR_3-(CH_2)_n-N^+R_6R_7R_8$; and $-O-(CH_2)_n-N^+R_6R_7R_8$.

Z is a functional group capable of chelating iron salts such as OH; $NHNR_9R_{10}$ (hydrazine), $NHOC(O)R_{11}$ (O-Acyl hydroxylamine), $N(OH)-C(O)R_{11}$ (N-acyl hydroxylamine), OOH, $SR_{12}$; 2-aminopyridine; 3-aminopyridine; $-NR_3-(CH_2)_n-NR_4R_5$; $-NR_3-(CH_2)_n-OH$; where:

$R_9$ and $R_{10}$, identical or different, are selected from the group consisting of H, $(C_1-C_6)$-alkyl, aryl and $(C_1-C_6)$-alkyl-aryl;

$R_{11}$ is selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl;

$R_{12}$ is selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl; and n=0, 2, 3, 4, 5 or 6.

Advantageously, the 9- and/or 11- and/or 20-amino derivatives of salinomycine, enantiomers, mixture of enantiomers, diastereoisomers and mixture of diasteroisomers of the invention are of formula (I):

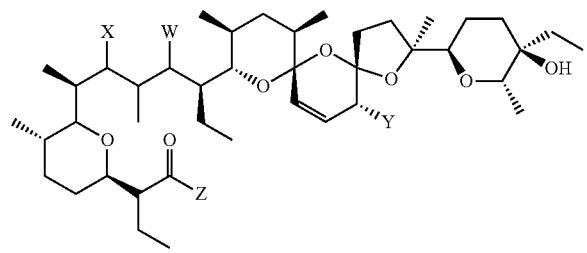

wherein:

W is selected from the group consisting of =O; $-NR_1R_2$, $-NR_3-(CH_2)_n-NR_4R_5$, $-O-(CH_2)_n-NR_4R_5$; $-NR_3-(CH_2)_n-N^+R_6R_7R_8$; and $-O-(CH_2)_n-N^+R_6R_7R_8$;

X is selected from the group consisting of =O, OH; $-NR_1R_2$; $-NR_3-(CH_2)_n-NR_4R_5$; $-O-(CH_2)_n-NR_4R_5$; $-NR_3-(CH_2)_n-N^+R_6R_7R_8$; and $-O-(CH_2)_n-N^+R_6R_7R_8$, Y is selected from the group consisting of OH; $-NR_1R_2$; $-NR_3-(CH_2)_n-NR_4R_5$; $-O-(CH_2)_n-NR_4R_5$; $-NR_3-(CH_2)_n-N^+R_6R_7R_8$; and $-O-(CH_2)_n-N^+R_6R_7R_8$, $R_1$ and $R_2$, identical or different, are selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl; or $R_1$ represents H and $R_2$ represents $OR_9$, where $R_9$ is H, $(C_1-C_6)$-alkyl, aryl and $(C_1-C_6)$-alkyl-aryl;

$R_3$ is selected from the group consisting of H; $(C_1-C_6)$-alkyl; $(C_1-C_6)$-alkyl-aryl;

$R_4$ and $R_5$, identical or different, are selected from the group consisting of H; $(C_1-C_6)$-alkyl; aryl; $(C_1-C_6)$-alkyl-aryl;

$R_6$, $R_7$ and $R_8$, identical or different, are selected from the group consisting of $(C_1-C_6)$-alkyl; aryl; $(C_1-C_6)$-alkyl-aryl;

n=2, 3, 4, 5 or 6, with the proviso that at least one of W, X and Y is selected from the group consisting of $-NR_1R_2$; $-NR_3-(CH_2)_n-NR_4R_5$, $-O-(CH_2)_n-NR_4R_5$; $-NR_3-(CH_2)_n-N^+R_6R_7R_8$; and $-O-(CH_2)_n-N^+R_6R_7R_8$.

Z is a functional group capable of chelating iron salts such as OH; $NHNR_9R_{10}$ (hydrazine), $NHOC(O)R_{11}$ (O-Acyl hydroxylamine), $N(OH)-C(O)R_{11}$ (N-acyl hydroxylamine), OOH, $SR_{12}$; 2-aminopyridine; 3-aminopyridine; $-NR_3-(CH_2)_n-NR_4R_5$; $-NR_3-(CH_2)_n-OH$; where:

$R_9$ and $R_{10}$, identical or different, are selected from the group consisting of H, $(C_1-C_6)$-alkyl, aryl and $(C_1-C_6)$-alkyl-aryl;

$R_{11}$ is selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl;

$R_{12}$ is selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl.

Advantageously, n=0, 2, 3 or 4.

Advantageously, W and/or X and/or Y are selected from the group consisting of $-NR_1R_2$; $-NR_3-(CH_2)_n-NR_4R_5$, $-O-(CH_2)_n-NR_4R_5$, more advantageously $-NR_1R_2$.

Advantageously, $R_1$ and $R_2$, identical or different, are selected from the group consisting of H; $(C_1-C_{16})$-alkyl, advantageously $(C_3-C_{14})$-alkyl, more advantageously $(C_8-C_{14})$-alkyl; $(C_3-C_{16})$-alkenyl, advantageously $(C_3-C_5)$-alkenyl; $(C_3-C_{16})$-alkynyl, advantageously $(C_3-C_5)$-alkynyl; $(C_3-C_{16})$-cycloalkyl, advantageously $(C_3-C_6)$-cycloalkyl; and $(C_1-C_6)$-alkyl-heteroaryl, advantageously $CH_2$-pyridynyl.

$R_1$ and $R_2$, identical or different, can also be selected from the group consisting of H; $(C_1-C_{16})$-alkyl, advantageously $(C_8-C_{14})$-alkyl; $(C_3-C_{16})$-alkynyl, advantageously $(C_3-C_5)$-alkynyl; and $(C_1-C_6)$-alkyl-heteroaryl, advantageously $CH_2$-pyridynyl.

Advantageously, $R_1$ and $R_2$ are not both H.

More advantageously, $R_1$ is H and $R_2$ is selected from the group consisting of $(C_1-C_{16})$-alkyl, advantageously $(C_3-C_{14})$-alkyl, more advantageously $(C_8-C_{14})$-alkyl; $(C_3-C_{16})$-alkenyl, advantageously $(C_3-C_5)$-alkenyl; $(C_3-C_{16})$-alkynyl, advantageously $(C_3-C_5)$-alkynyl; $(C_3-C_{16})$-cycloalkyl, advantageously $(C_3-C_6)$-cycloalkyl; and $(C_1-C_6)$-alkyl-heteroaryl, advantageously $CH_2$-pyridynyl.

$R_1$ can also be H and $R_2$ can also be selected from the group consisting of $(C_1-C_{16})$-alkyl, advantageously $(C_8-C_{14})$-alkyl; and $(C_3-C_{16})$-alkynyl, advantageously $(C_3-C_5)$-alkynyl; and $(C_1-C_6)$-alkyl-heteroaryl, advantageously $CH_2$-pyridynyl.

Advantageously, $R_3$ is selected from the group consisting of H and $(C_1-C_6)$-alkyl. Preferably, $R_3$ is H.

Advantageously, $R_4$ and $R_5$, identical or different, are selected from the group consisting of H and $(C_1-C_{16})$-alkyl. More advantageously, $R_4$ and $R_5$ are H or $(C_1-C_6)$-alkyl. Preferably, $R_4$ and $R_5$ are identical. In one advantageous embodiment, the group $-(CH_2)_n-NR_4R_5$ is selected from the group consisting of $-(CH_2)_2-N(CH_3)_2$, $-(CH_2)_3-N(CH_3)_2$, $-(CH_2)_2-NH_2$ and $-(CH_2)_3-NH_2$.

Advantageously, $R_6$, $R_7$ and $R_8$, identical or different, are selected from the group consisting of $(C_1-C_6)$-alkyl; and aryl. More advantageously, $R_6$, $R_7$ and $R_8$ are $(C_1-C_6)$-alkyl. Preferably, $R_6$, $R_7$ and $R_8$ are identical. In one advantageous embodiment, the group $-(CH_2)_n-N^+R_6R_7R_8$ is selected from the group consisting of $-(CH_2)_2-N^+(CH_3)_3$, and $-(CH_2)_3-N^+(CH_3)_3$.

Advantageously, Z is OH, OOH, $NHNH_2$, NHOH, or $NH_2OH$, preferably OH. In another particular embodiment, Z is SH.

In a first embodiment according to the present invention, the compound is a 9-, 11-, 20-triamino derivative of salinomycine, an enantiomer, a mixture of enantiomers, a diastereoisomer and a mixture of diastereoisomers thereof of formula (Ia):

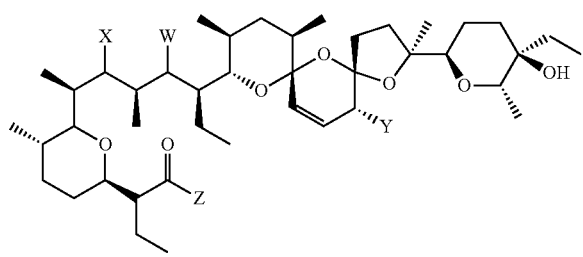

where W, X, Y, Z, $R_1$, $R_2$, $R_3$, $R_4$, $R_5$, $R_6$, $R_7$, $R_8$ and n are as defined in formula (I).

In a second embodiment according to the present invention, the compound is a diamino derivative of salinomycine, wherein two of W, X and Y are selected from the group consisting of —$NR_1R_2$; —$NR_3$—$(CH_2)_n$—$NR_4R_5$; —O—$(CH_2)_n$—$NR_4R_5$; —$NR_3$—$(CH_2)_n$—$N^+R_6R_7R_8$; and —O—$(CH_2)_n$—$N^+R_6R_7R_8$ of formula (Ib), where W, X, Y, Z, $R_1$, $R_2$, $R_3$, $R_4$, $R_5$, $R_6$, $R_7$, $R_8$ and n are as defined in formula (I).

The compound of formula (Ib) may be a 9-, 20-diamino derivative of salinomycine, an enantiomer, a mixture of enantiomers, a diastereoisomer and a mixture of diastereoisomers thereof of formula (Ib1):

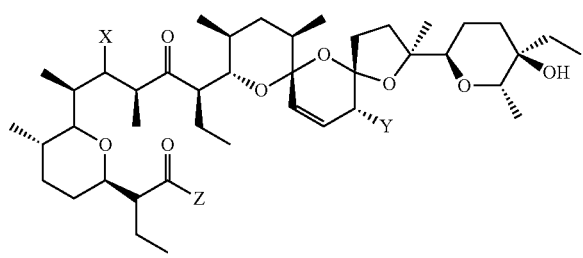

wherein X and Y, identical or different, are selected from the group consisting of —$NR_1R_2$; —$NR_3$—$(CH_2)_n$—$NR_4R_5$, —O—$(CH_2)_n$—$NR_4R_5$; —$NR_3$—$(CH_2)_n$—$N^+R_6R_7R_8$; and —O—$(CH_2)_n$—$N^+R_6R_7R_8$, and Z, $R_1$, $R_2$, $R_3$, $R_4$, $R_5$, $R_6$, $R_7$, $R_8$ and n are as defined in formula (Ib).

The compound of formula (Ib) may be a 9-, 11-diamino derivative of salinomycine, an enantiomer, a mixture of enantiomers, a diastereoisomer and a mixture of diastereoisomers thereof of formula (Ib2):

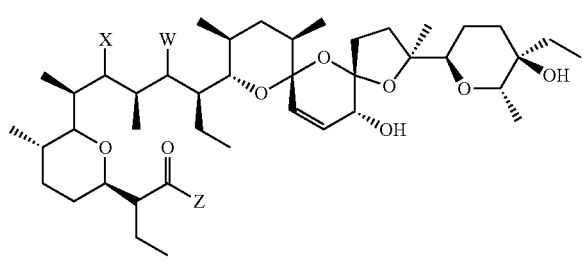

wherein W and X, identical or different, are selected from the group consisting of —$NR_1R_2$; —$NR_3$—$(CH_2)_n$—$NR_4R_5$, —O—$(CH_2)_n$—$NR_4R_5$; —$NR_3$—$(CH_2)_n$—$N^+R_6R_7R_8$; and —O—$(CH_2)_n$—$N^+R_6R_7R_8$, and Z, $R_1$, $R_2$, $R_3$, $R_4$, $R_5$, $R_6$, $R_7$, $R_8$ and n are as defined in formula (Ib), The compound of formula (Ib) may be an 11-, 20-diamino derivative of salinomycine, an enantiomer, a mixture of enantiomers, a diastereoisomer and a mixture of diastereoisomers thereof of formula (Ib3):

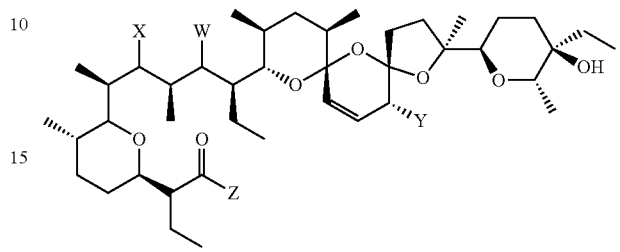

wherein W and Y, identical or different, are selected from the group consisting of —$NR_1R_2$; —$NR_3$—$(CH_2)_n$—$NR_4R_5$, —O—$(CH_2)_n$—$NR_4R_5$; —$NR_3$—$(CH_2)_n$—$N^+R_6R_7R_8$; and —O—$(CH_2)_n$—$N^+R_6R_7R_8$, X is OH or =O, and Z, $R_1$, $R_2$, $R_3$, $R_4$, $R_5$, $R_6$, $R_7$, $R_8$ and n are as defined in formula (Ib).

In an advantageous embodiment according to the present invention, the compound of formula (I) is a monoamine derivative of salinomycine of formula (Ic), and only one of W, X or Y is a —$NR_1R_2$; —$NR_3$—$(CH_2)_n$—$NR_4R_5$; —O—$(CH_2)_n$—$NR_4R_5$; —$NR_3$—$(CH_2)_n$—$N^+R_6R_7R_8$; or —O—$(CH_2)_n$—$N^+R_6R_7R_8$ group, and W, X, Y, Z, $R_1$, $R_2$, $R_3$, $R_4$, $R_5$, $R_6$, $R_7$, $R_8$ and n are as defined in formula (I).

The compound of formula (Ic) may be a 9-amino derivative of salinomycine of formula (Ic1):

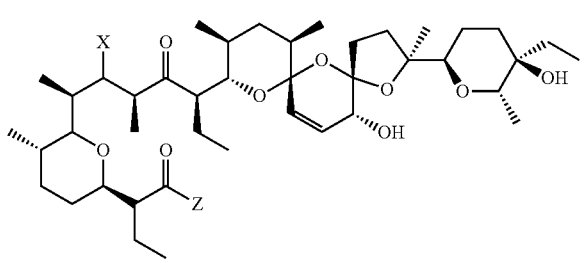

wherein:

X is selected from the group consisting of —$NR_1R_2$; —$NR_3$—$(CH_2)_n$—$NR_4R_5$; —O—$(CH_2)_n$—$NR_4R_5$; —$NR_3$—$(CH_2)_n$—$N^+R_6R_7R_8$; and —O—$(CH_2)_n$—$N^+R_6R_7R_8$; and Z, $R_1$, $R_2$, $R_3$, $R_4$, $R_5$, $R_6$, $R_7$, $R_8$ and n are as defined in formula (Ic).

Advantageously, Z is OH.

The inventors have indeed discovered that the presence of an amino group and the carboxylic acid at position 1 result I compounds having an improved activity against CSCs and TICs.

The compound of formula (Ic) may be a 11-amino derivative of salinomycine of formula (Ic2):

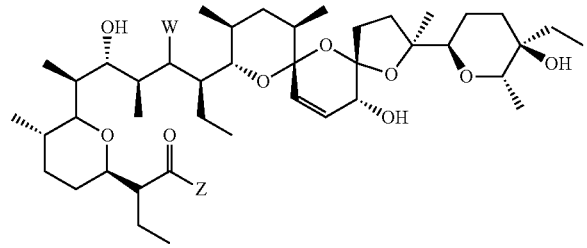

wherein:

W is selected from the group consisting of —NR₁R₂; —NR₃—(CH₂)ₙ—NR₄R₅;    —O—(CH₂)ₙ—NR₄R₅; —NR₃—(CH₂)ₙ—N⁺R₆R₇R₈;   and   —O—(CH₂)ₙ—N⁺R₆R₇R₈; and Z, R₁, R₂, R₃, R₄, R₅, R₆, R₇, R₈ and n arep as defined in formula (Ic).

The compound of formula (Ic) may advantageously be a 20-amino derivative of salinomycine of formula (Ic3):

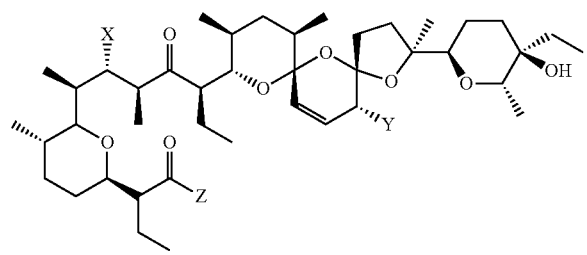

wherein:

X is selected from the group consisting of OH and =O,

Y is selected from the group consisting of —NR₁R₂; —NR₃—(CH₂)ₙ—NR₄R₅;    —O—(CH₂)ₙ—NR₄R₅; —NR₃—(CH₂)ₙ—N⁺R₆R₇R₈;   and   —O—(CH₂)ₙ—N⁺R₆R₇R₈; and Z, R₁, R₂, R₃, R₄, R₅, R₆, R₇, R₈ and n are as defined in formula (I).

In one advantageous embodiment, in the compounds of formula (Ic3), X is OH, Z is OH, and Y is —NR₁R₂. More advantageously, R₁ is H and R₂ is selected from the group consisting of (C₁-C₁₆)-alkyl, advantageously (C₈-C₁₄)-alkyl; (C₃-C₁₆)-alkenyl, advantageously (C₃-C₅)-alkenyl; (C₃-C₁₆)-alkynyl, advantageously (C₃-C₅)-alkynyl; (C₃-C₁₆)-cycloalkyl, advantageously (C₃-C₆)-cycloalkyl; and (C₁-C₆)-alkyl-heteroaryl, advantageously CH₂-pyridynyl.

The inventors have indeed discovered that the presence of an amino group and the carboxylic acid at position 1 result I compounds having an improved activity against CSCs and TICs.

In another embodiment, X is =O, Y is selected from the group consisting of =N—OH and NR₁R₂ and Z is NHOH. Advantageously, X is =O, Y is NR₁R₂ and Z is NHOH. More advantageously, R₁ is H and R₂ is CH₂-pyridinyl, preferably CH₂-(2-pyridinyl). Alternatively, R₁ is H and R₂ is (C₃-C₁₆)-cycloalkyl, and (C₃-C₁₆)-alkynyl.

In a particular embodiment, when Z is —NHOH, W is =O and X is —OH, then Y is not a propargyl group.

In a particular embodiment, when Z is —OH, W is =O and X is OH, then Y is not NCH₂CH₂N(CH₃)₂.

The compounds of formula (I) may advantageously be chosen from the group consisting of:

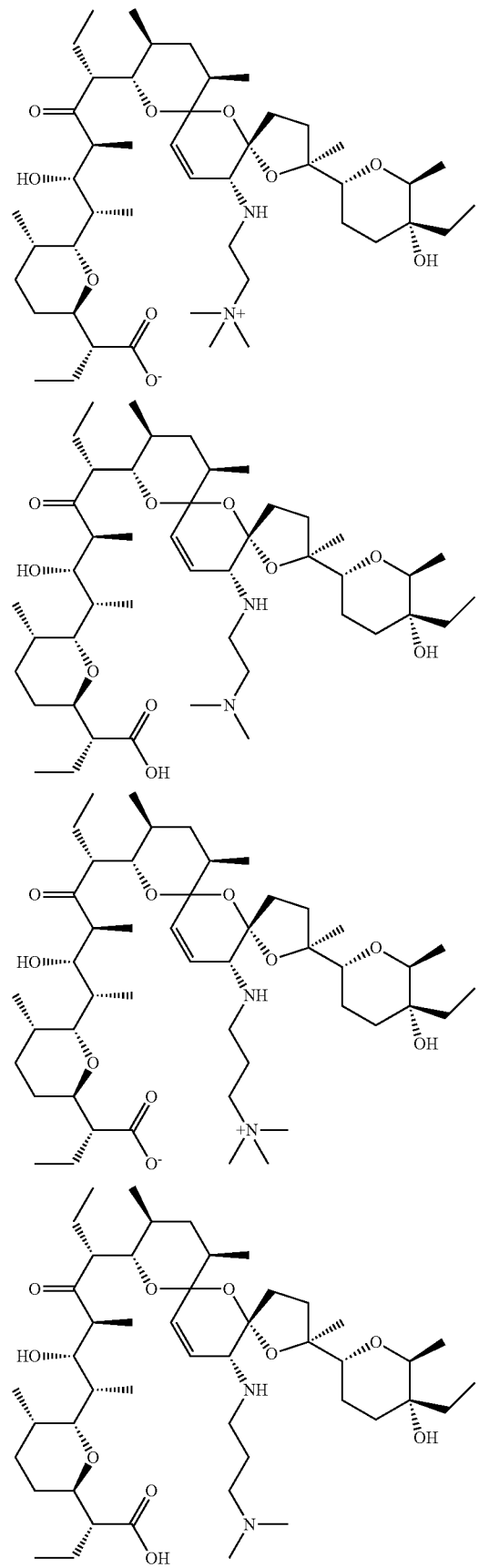

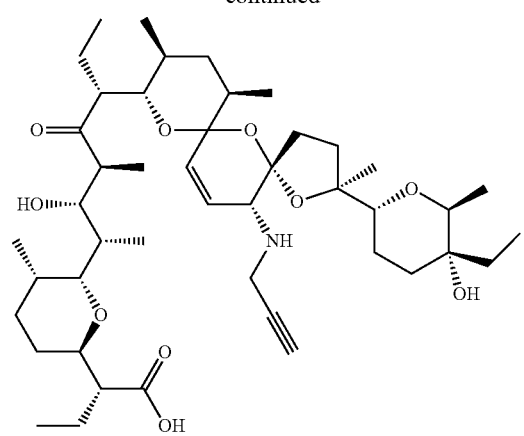
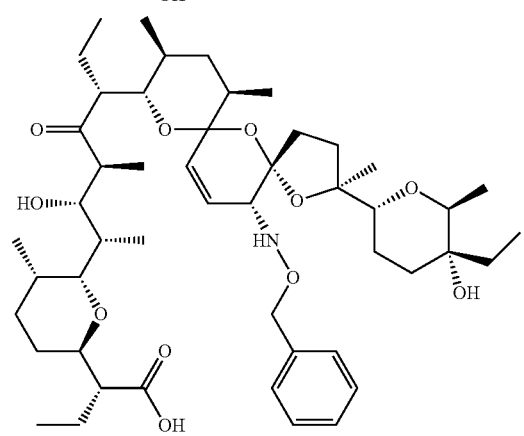
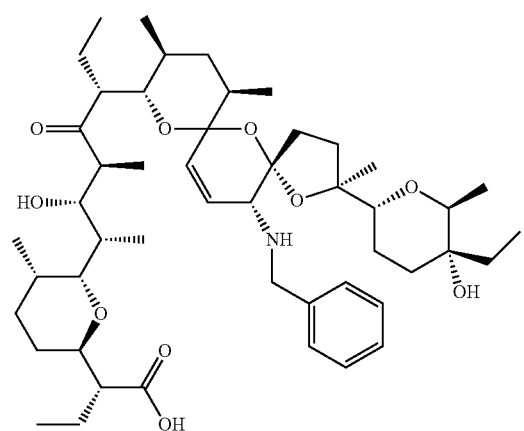
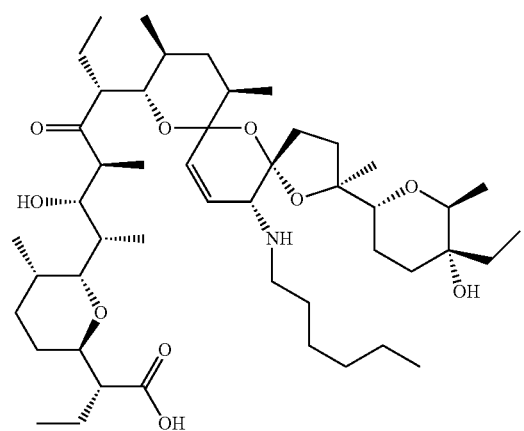
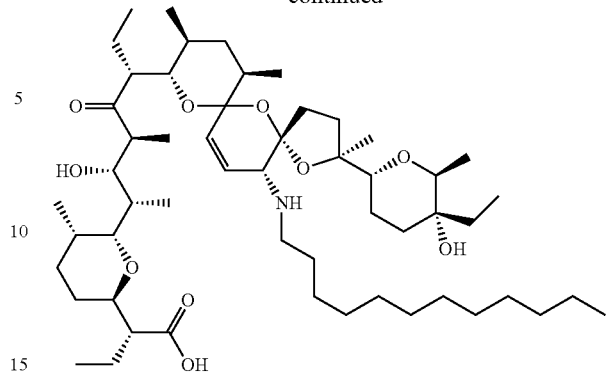
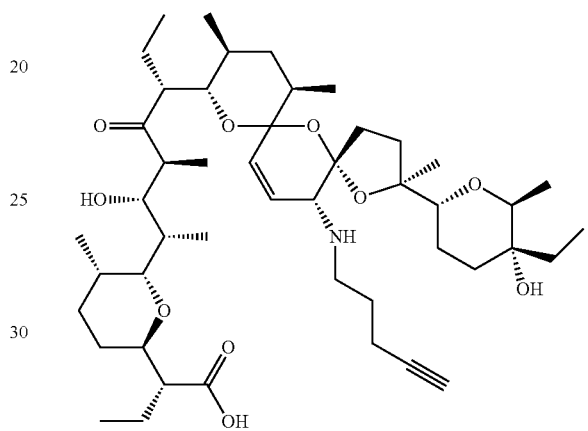
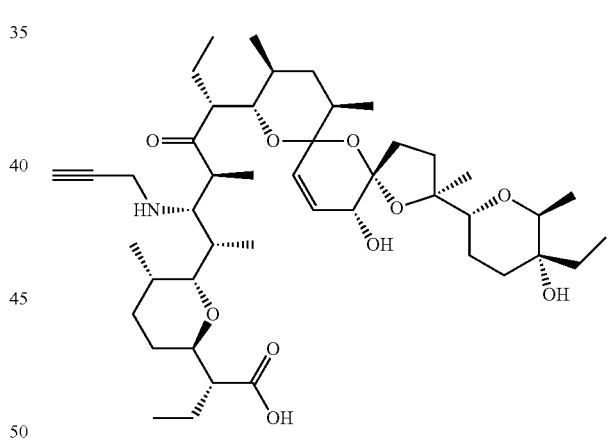
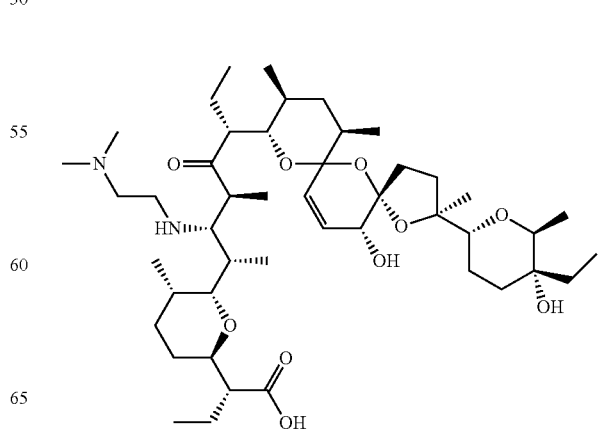

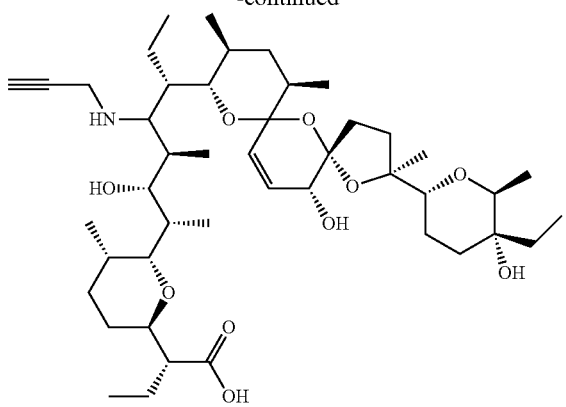
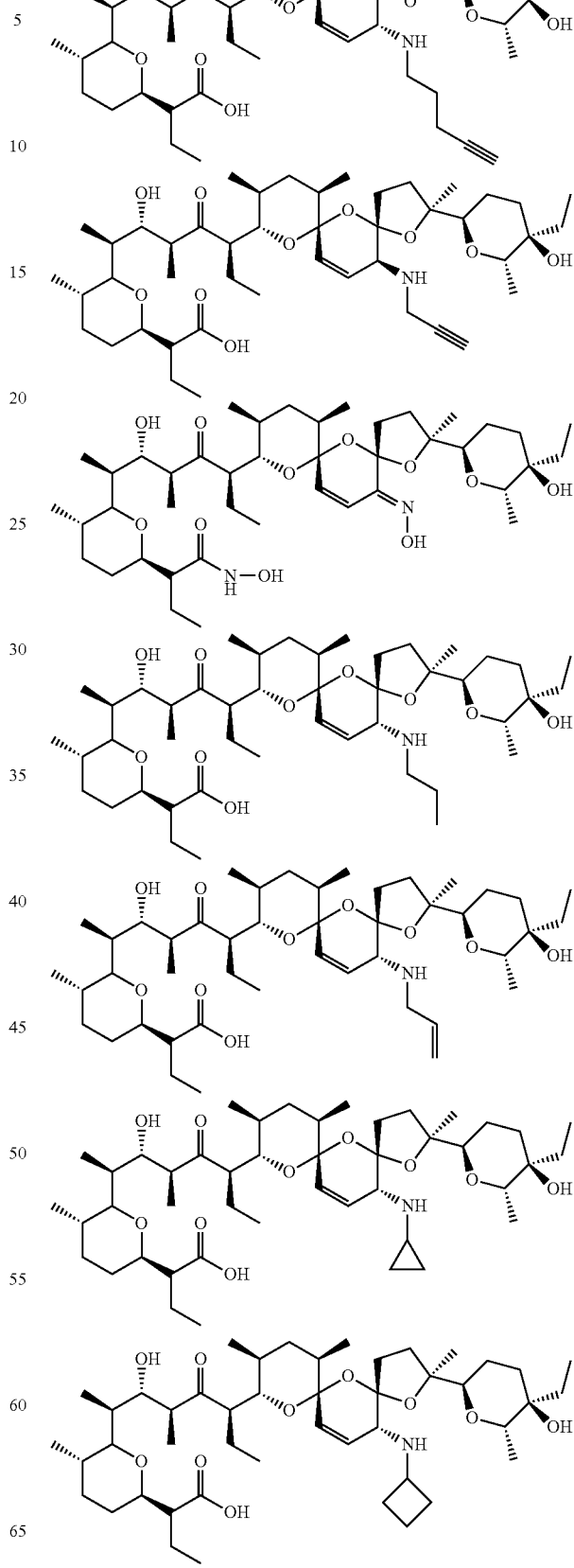

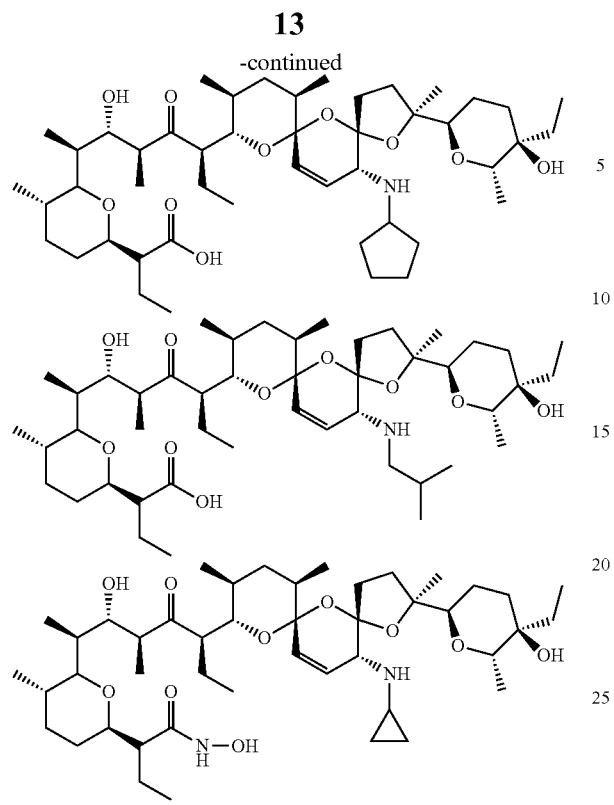
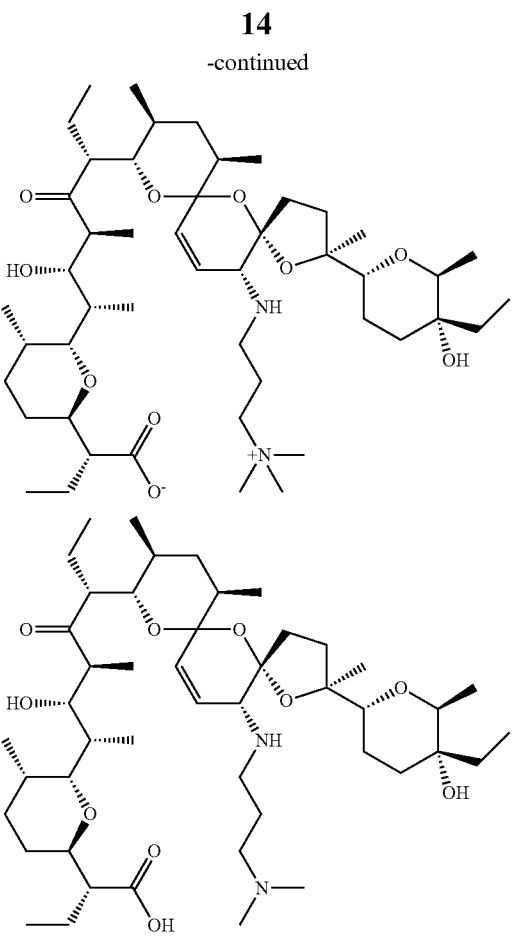
The compounds of formula (I) can be chosen from the group consisting of:
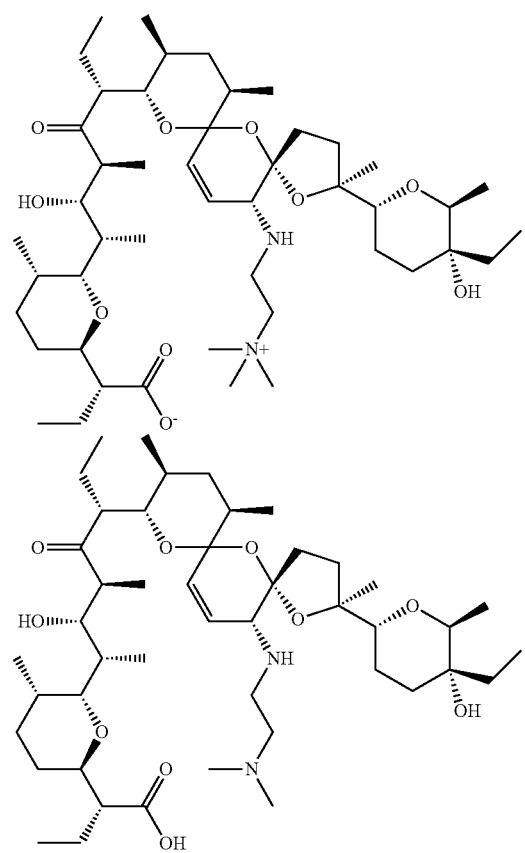

-continued
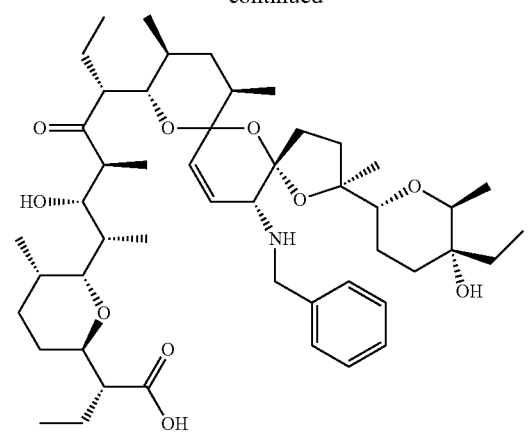
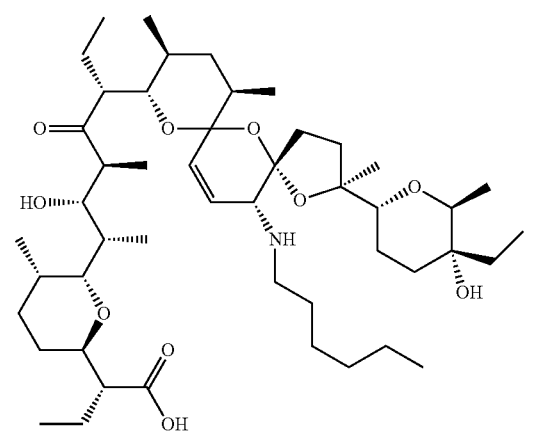
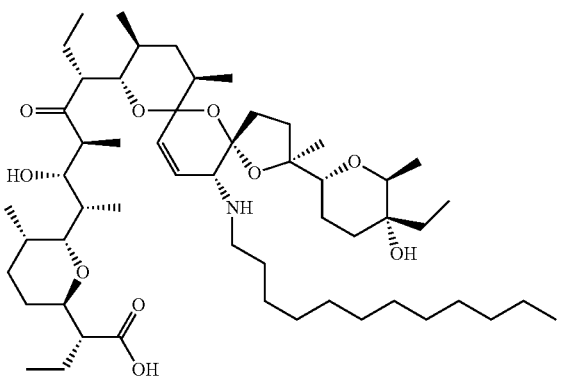
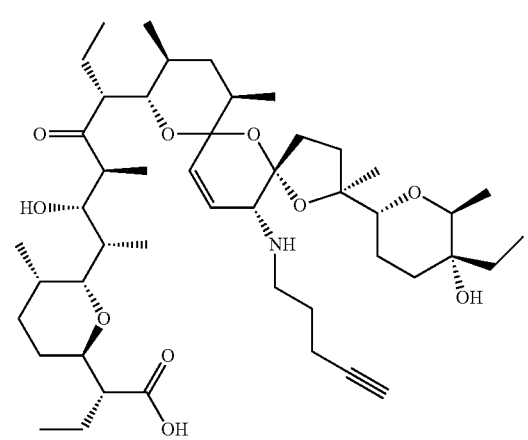
-continued
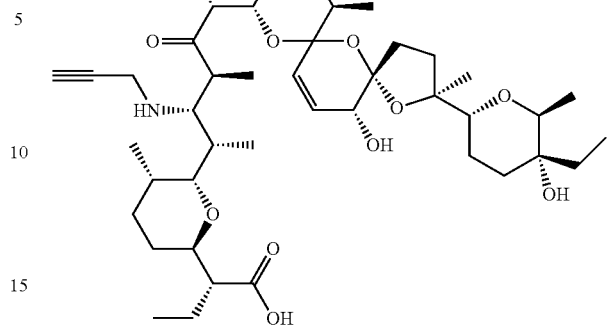
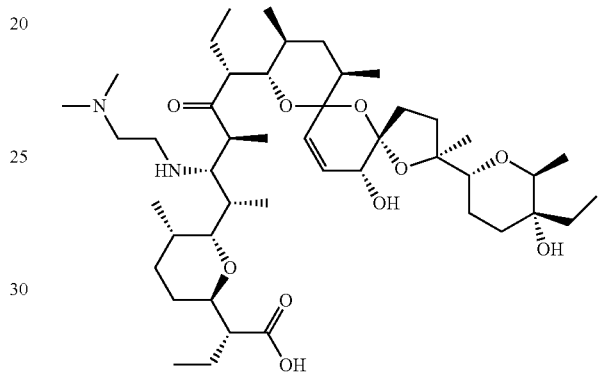
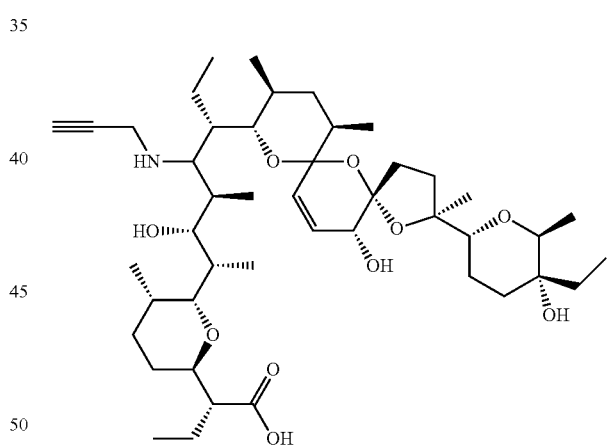
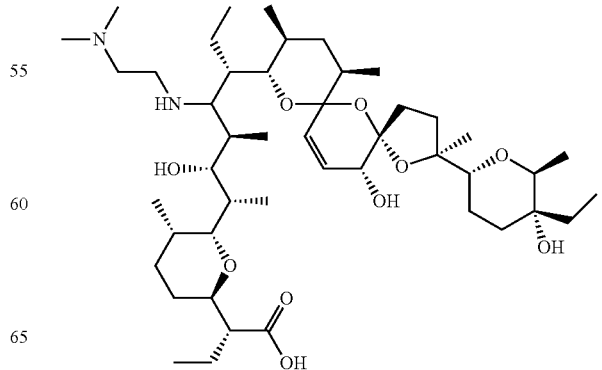

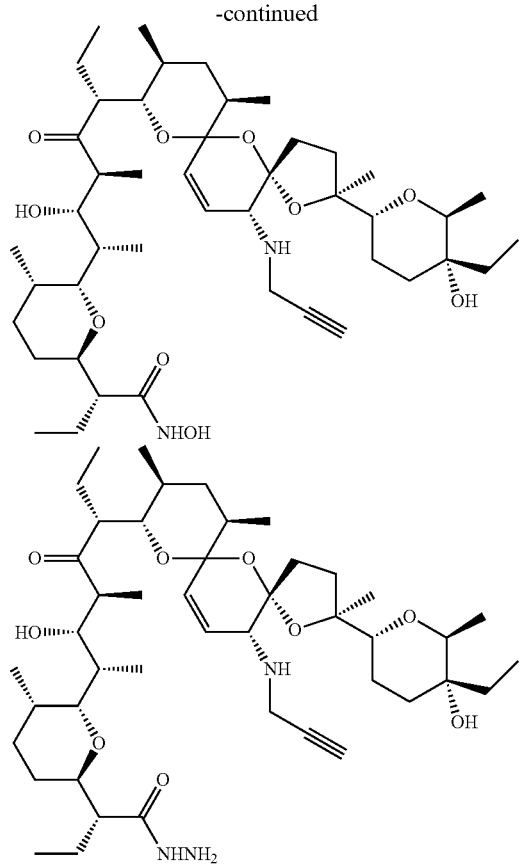

In a particular embodiment, W is =O, X is —OH, Y is —NR$_1$R$_2$ preferably with R$_1$ being H and R$_2$ being (C$_3$-C$_{16}$)-cycloalkyl, preferably cyclopropyl, and Z is —OH.

In a particular embodiment, W is =O, X is OH, Y is —NR$_1$R$_2$ preferably with R$_1$ being H and R$_2$ being (C$_3$-C$_{16}$)-alkynyl, preferably propargyl, and Z is —OH.

The invention also concerns a pharmaceutical composition comprising at least one compound of formula (I) as defined previously, a pharmaceutically acceptable salt, solvate or hydrate thereof, and at least one pharmaceutically acceptable excipient.

The pharmaceutical composition can further comprise at least one other anticancer drug, such as Adriamycin and Cyclophosphamide (AC), Docetaxel (Taxol), Trastuzumab, Degarelix, Capecitabine, ifosfamide or Cis platine. Advantageously, the pharmaceutical composition further comprises Adriamycin and cyclophosphamide (AC) or docetaxel (Taxol).

The pharmaceutical compositions of the invention can be intended to oral, sublingual, subcutaneous, intramuscular, intravenous, transdermal, topical or rectal administration. The active ingredient can be administered in unit forms for administration, mixed with conventional pharmaceutical carriers, to animals or to humans.

When a solid composition is prepared in the form of tablets, the main active ingredient is mixed with a pharmaceutical vehicle and other conventional excipients known to those skilled in the art.

The compounds of the invention can be used in a pharmaceutical composition at a dose ranging from 0.01 mg to 1000 mg a day, administered in only one dose once a day or in several doses along the day, for example twice a day. The daily administered dose is advantageously comprised between 5 mg and 500 mg, and more advantageously between 10 mg and 200 mg. However, it can be necessary to use doses out of these ranges, which could be noticed by the person skilled in the art.

It has been shown that salinomycin, in addition to resulting in an inhibition of proliferation or an induction of apoptosis in CSCs and TICs in a variety of cancer types including breast, blood, lung, pancreas and colon cancers, hampers migration of these cells.

The present invention therefore concerns a compound of formula (I) as defined above or a pharmaceutical composition as defined above for use as a drug. The present invention further concerns a compound of formula (I) as defined above or a pharmaceutical composition as defined above for use in the treatment of cancer, such as carcinoma, sarcoma, metastatic disorders, prostate, colon, lung, breast, liver cancer, and leukemias, advantageously breast cancer and/or for the prevention of cancer relapse and/or metastases.

Another aspect of the present invention relates to the use of a compound of formula (I) as defined above or a pharmaceutical composition as defined above, for the manufacture of a medicament, advantageously for use in the treatment of cancer, such as carcinoma, sarcoma, metastatic disorders, prostate, colon, lung, breast, liver cancer, and leukemias, advantageously breast cancer, and/or in the prevention of cancer relapse and/or metastases.

A further aspect of the invention relates to a method of treatment of cancer, such as carcinoma, sarcoma, metastatic disorders, prostate, colon, lung, breast, liver cancer, and leukemias, advantageously breast cancer and/or prevention of cancer relapse and/or metastases, comprising the administration of a therapeutically effective amount of a compound of formula (I) as defined above or a pharmaceutical composition as defined above to a person in need thereof.

The compound of formula (I) as defined above may be administered alone or in combination with a therapy against cancer, for example with other anticancer drugs. Anticancer drugs are known in the art.

Therefore, a further aspect of the invention relates to a pharmaceutical product comprising: a) the compound of formula (I) as defined above, and b) another chemotherapy compound, such as Adriamycin and Cyclophosphamide (AC), Docetaxel (Taxol), Trastuzumab, Degarelix, Capecitabine, ifosfamide or Cis platine, advantageously Adriamycin and Cyclophosphamide (AC), Docetaxel (Taxol), as combination product for simultaneous, separate or staggered use as a medicament, in particular in the treatment of cancer, advantageously breast cancer.

By the phrase "combination product" is meant herein the compound of formula (I) of the present invention is administered to the individual thus treated before, during (including concurrently with-preferably co-formulated with) and/or after treatment of an individual with the other anti-cancer drug. The formulations may conveniently be presented in unit dosage form by methods known to those skilled in the art. Preferably, the kit-of-parts contains instructions indicating the use of the dosage form to achieve a desirable affect and the amount of dosage form to be taken over a specified time period. Preferably, said combination product is for the treatment of cancer such as carcinoma, sarcoma, metastatic disorders, prostate, colon, lung, breast, liver cancer, and leukemias, advantageously breast cancer, and/or in the prevention of cancer relapse and/or metastases.

Since the compounds of formula (I) as defined above are capable of inhibiting autophagy, the present invention also concerns a compound of formula (I) for use in the treatment of diseases in which autophagy is involved, in particular malaria.

Another aspect of the present invention relates to the use of a compound of formula (I) as defined above, for the manufacture of a medicament, advantageously for use in the treatment of diseases in which autophagy is involved, in particular malaria.

A further aspect of the invention relates to a method of treatment of diseases in which autophagy is involved, in particular malaria, comprising the administration of a therapeutically effective amount of a compound of formula (I) as defined above to a person in need thereof.

The compounds of formula (I) can be prepared following the methods illustrated in Scheme 1 and described thereafter:

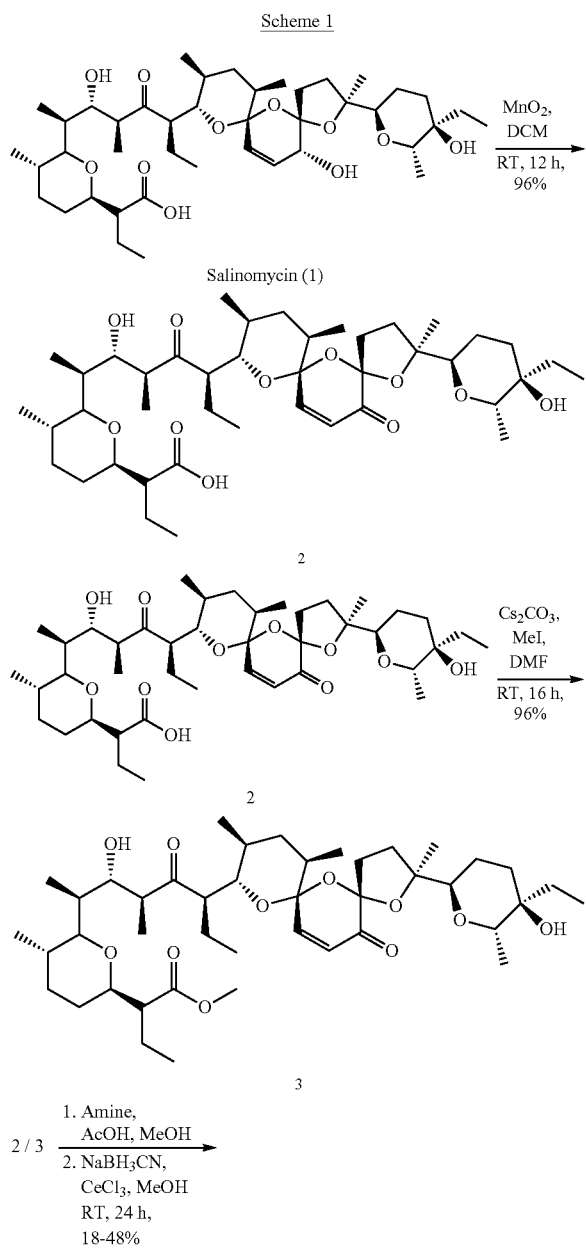

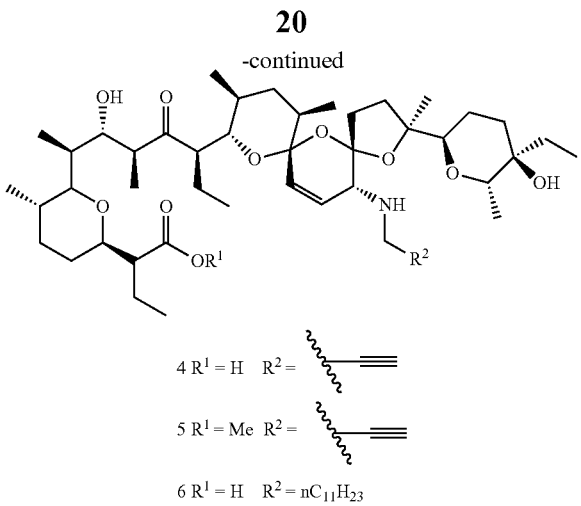

The $NR_1R_2$; $-NR_3-(CH_2)_n-NR_4R_5$ and $-NR_3-(CH_2)_n-N^+R_6R_7R_8$ group at position 20 of salinomycine can be introduced by the following method:

(a) oxidizing the allylic alcohol at position 20 of salinomycine to the α,β-unsaturated ketone.

Methods for the oxidation of allylic alcohols are known in the art. Advantageously, this oxidation is performed with $MnO_2$.

(b) protecting the carboxylic acid at position 1 of the α,β-unsaturated ketone analog of salinomycine, Any suitable protecting group for carboxylic acids may be used. Advantageously, the carboxylic acid is protected in the form of an ester, such as a methyl ester or an allyl ester. The carboxylic acid at position 1 may also be protected prior to the oxidation to the α,β-unsaturated ketone.

Suitable protecting groups are for example disclosed in Greene, "Protective Groups In Organic synthesis", (John Wiley & Sons, New York (1981).

(c) reacting the α,β-unsaturated ketone with an amine and simultaneously or subsequently reducing the imine, Methods for preparing amines by reductive amination are known in the art. Advantageously, the imine is formed by reacting the amine in a polar solvent in the presence of an acid. In a particular embodiment, the imine is formed in a mixture of an alcohol, such as methanol or ethanol and acetic acid. The reduction of the imine into the amine is advantageously done with a borohydride, such as sodium borohydride or sodium cyanoborohydride, in the presence of a cerium salt, such as cerium trichloride $CeCl_3$.

(d) deprotecting the ester at position 1 to provide the carboxylic acid.

Methods for the deprotection of an ester are for example disclosed in Greene, "Protective Groups In Organic synthesis", (John Wiley & Sons, New York (1981).

The $NR_1R_2$; $-NR_3-(CH_2)_n-NR_4R_5$ and $-NR_3-(CH_2)_n-N^+R_6R_7R_8$ group at position 11 can be obtained by reacting the keto-group at position 11 with an amine and simultaneous or subsequent reduction of the imine.

Methods for preparing amines by reductive amination are known in the art. Advantageously, the imine is formed by reacting the amine in a polar solvent in the presence of an acid. In a particular embodiment, the imine is formed in a mixture of an alcohol, such as methanol or ethanol and acetic acid. The reduction of the imine into the amine is advantageously done with a borohydride, such as sodium borohydride or sodium cyanoborohydride.

The carboxylic acid and/or hydroxyl groups of salinomycine, when present, may be protected. Suitable protecting groups are for example disclosed in Greene, "Protective Groups In Organic synthesis", (John Wiley & Sons, New York (1981). Advantageously, the protecting group is a triethylsilyl group.

The $NR_1R_2$; —$NR_3$—$(CH_2)_n$—$NR_4R_5$ and —$NR_3$—$(CH_2)_n$—$N^+R_6R_7R_8$ group at position 9 can be introduced by the following steps:

(a) protecting the hydroxyl groups at positions 11, 20 and 28 of salinomycine, (b) transforming the hydroxyl group at position 9 into a leaving group, The leaving group may be, for example, a sulfonate, such as a mesylate or a trifluoromethylsulfonate. Methods for the substitution of an hydroxyl group with an amine are known in the art.

(c) reacting the product obtain in step (b) with an appropriate amine, (e) deprotecting the hydroxyl groups and the carboxylic acid.

The groups —O—$(CH_2)_n$—$NR_4R_5$ and —O—$(CH_2)_n$—$N^+R_6R_7R_8$ can be introduced starting from the 9, 11 and/or 20 hydroxyl analogs of salinomycine.

The hydroxyl group at position 11 of salinomycine can be obtained by reducing the keto-group at this position using methods known in the art. The ketone may for example be reduced with sodium borohydride in an alcohol, such as methanol or ethanol.

The reaction is performed by the following steps:

(a) protecting the carboxylic acid at position 1 and the hydroxyl groups at position 9, 11 and/or 20, when present, and the hydroxyl group at position 28, Advantageously, the carboxylic acid is protected as an allyl ester.

(b) transforming the hydroxyl group into a leaving group,

The leaving group may be, for example, a sulfonate, such as a mesylate or a trifluoromethylsulfonate. Methods for transforming an hydroxyl group into a leaving one are known in the art. The reaction is preferably conducted in the presence of a base, such as pyridine.

(c) reacting the product obtained in step (b) with a compound of formula HO—$(CH_2)_n$—$NR_4R_5$ or HO—$(CH_2)_n$—$N^+R_6R_7R_8$ in the presence of a base, Advantageously, the reaction is performed with a strong base, such as sodium hydride. Preferably, the alkoxide is prepared separately, prior to being reacted with the product obtained in step (b).

(d) deprotecting the optionally protected hydroxyl groups and the carboxylic acid.

The present invention therefore also concerns a process for preparing a 20-amino, 9-, 20-diamino or 9-, 11-,20-triamino derivative of salinomycine of formula (I), wherein Y is selected from the group consisting of —$NR_1R_2$; —$NR_3$—$(CH_2)_n$—$NR_4R_5$; and —$NR_3$—$(CH_2)_n$—$N^+R_6R_7R_8$; where $R_1$, $R_2$, $R_3$, $R_4$, $R_5$, $R_6$, $R_7$, $R_8$ and n are as defined for formula (I), comprising the steps of:

(a) reacting a compound of formula (II):

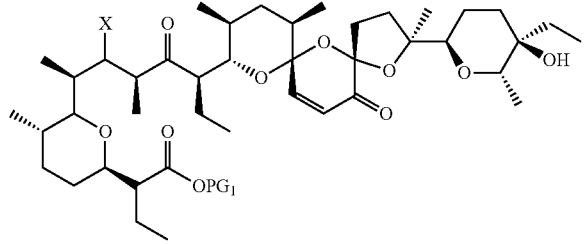

wherein:

X is as defined in claim 1, optionally protected, $PG_1$ is a carboxylic acid protective group, advantageously methyl, with an amine of formula $R_2NH_2$, or $NH_2$—$(CH_2)_n$—$NR_4R_5$; or $NH_2$—$(CH_2)_n$—$N^+R_6R_7R_8$;

(b) reducing the imine obtained in step (a), advantageously with a borohydride, in the presence of a cerium salt such as cerium trichloride, (c) deprotecting the carboxylic acid at position 1, (d) optionally alkylating the amine.

The present invention further concerns a process for preparing a 9-amino, a 9-,20-diamino or a 9-, 11-, 20-triamino derivative of salinomycine of formula (I), wherein Y is selected from the group consisting of —O—$(CH_2)_n$—$NR_4R_5$ and —O—$(CH_2)_n$—$N^+R_6R_7R_8$; where $R_4$, $R_5$, $R_6$, $R_7$, $R_8$ and n are as defined for formula (I), comprising the steps of:

(a) reacting a compound of formula (III):

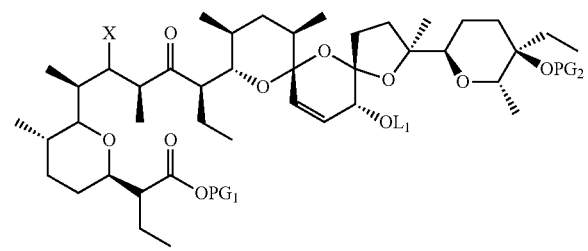

wherein:

X is as defined in formula (I), optionally protected, $OL_1$ is a leaving group, such as a sulfonate, advantageously a mesylate, $PG_1$ is a carboxylic acid protective group, such as methyl or allyl, advantageously allyl, $PG_2$ is an hydroxyl protecting group, advantageously triethylsilyl, with a compound of formula M-O—$(CH_2)_n$—$NR_4R_5$ or M-O—$(CH_2)_n$—$N^+R_6R_7R_8$, where:

M is a metal chosen from the group consisting of Na, K and Li, (b) deprotecting the carboxylic acid at position 1 and the hydroxyl groups.

Definitions:

The compounds of formula (I) in which X or Y is a —$NR_3$—$(CH_2)_n$—$N^+R_6R_7R_8$ or —O—$(CH_2)_n$—$N^+R_6R_7R_8$ group are betaines. In that case, the carboxylic acid at position 1 of salinomycine is in the form of the carboxylate, i.e. Z will be $O^-$ instead of OH.

Within the groups, radicals or fragments defined in the description and the claims, the number of carbon atoms is specified inside the brackets. For example, $(C_1$-$C_{16})$-alkyl designates an alkyl group or radical having 1 to 16 carbon atoms.

For the groups comprising two or more subgroups, the attachment is indicated with "—". For example, "—$(C_1$-$C_6)$-alkyl-aryl" indicates a radical alkyl bound to a radical aryl wherein the alkyl is bound to the rest of the molecule.

In the sense of the present invention, the expression "$(C_1$-$C_{16})$-alkyl" designates an optionally substituted acyclic, saturated, linear or branched hydrocarbon chain comprising 1 to 16 carbon atoms. Examples of $(C_1$-$C_{16})$-alkyl groups include methyl, ethyl, propyl, butyl, pentyl, hexyl, heptyl, octyl, and dodecyl. Unless explicitly stated, the definitions propyl, butyl, pentyl, hexyl, dodecyl, etc. include all possible isomers. For example, butyl comprises n-butyl, iso-butyl, sec-butyl and tert-butyl.

In the sense of the present invention, the expression "—($C_3$-$C_{16}$)-alkenyl" designates an optionally substituted acyclic, saturated, linear or branched hydrocarbon chain comprising 3 to 16 carbon atoms, at least two of which are linked via a double bond. Examples of "—($C_3$-$C_{16}$)-alkenyl" include propenyl, butenyl, pentenyl or hexenyl. Unless explicitly stated, the definitions of propenyl, butenyl, pentenyl and hexenyl include all possible isomers.

In the sense of the present invention, the expression "—($C_3$-$C_{16}$)-alkynyl" designates an optionally substituted acyclic, saturated, linear or branched hydrocarbon chain comprising 3 to 16 carbon atoms, at least two of which are linked via a triple bond. Examples of "—($C_3$-$C_{16}$)-alkynyl" include propynyl, butynyl, pentynyl or hexynyl. Unless explicitly stated, the definitions of propynyl, butynyl, pentynyl and hexynyl include all possible isomers.

In the sense of the present invention, the expression "($C_3$-$C_{16}$)-cycloalkyl" designates an optionally substituted cyclic, saturated hydrocarbon chain comprising 1 to 16 carbon atoms. Examples of ($C_3$-$C_{16}$)-cycloalkyl groups include cyclopropyl, cyclobutyl, cyclopentyl, cyclohexyl, cycloheptyl, cyclooctyl, and cyclododecyl. Advantageously, ($C_3$-$C_{16}$)-cycloalkyl group is selected from cyclopropyl, cyclobutyl and cyclopentyl.

The term "optionally substituted" as used herein means that any of the hydrogen atoms can be replaced by a substituent, such as fluorine.

The term "aryl" designates an aromatic, monocyclic ring that may be fused with a second saturated, unsaturated or aromatic ring. The term aryl include, without restriction to the following examples, phenyl, indanyl, indenyl, naphtyl, anthracenyl, phenanthrenyl, tetrahydronaphtyl, and dihydronaphtyl. The preferred aryl are those comprising one six-membered aromatic ring. The aryl group may be substituted with one or more groups independently selected from the group consisting of alkyl, alkoxy, halogen, hydroxyl, amino, nitro, cyano, trifluoro, carboxylic acid or carboxylic ester. Examples of substituted phenyl groups are methoxyphenyl, dimethoxyphenyl, trimethoxyphenyl, fluorophenyl and trifluoromethylphenyl.

The term "—($C_1$-$C_6$)-alkyl-aryl" designates in the sense of the present invention an aryl group, as defined above, linked to the rest of the molecule by an alkyl chain containing 1 to 6 carbon atoms. Advantageously, the ""—($C_1$-$C_6$)-alkyl-aryl is a substituted or unsubstituted benzyl. Examples of substituted benzyl groups include methoxybenzyl, cyanobenzyl, nitrobenzyl or fluorobenzyl.

The term heteroaryl designates a mono- or polycyclic aryl as defined above where one or more carbon atoms have been replaced with one or more heteroatoms selected from the group consisting of N, O and S. Unless explicitly stated, the term "heteroaryl" includes all possible isomers. Examples of heteroaryl groups include furyl, thienyl, imidazolyl, pyridyl, pyrrolyl, N-alkyl pyrrolyl, pyrimidinyl, pyrazinyl, tetrazolyl, triazolyl and triazinyl. The heteroaryl group may be substituted with one or more groups independently selected from the group consisting of alkyl, alkoxy, halogen, hydroxyl, amino, nitro, cyano, trifluoro, carboxylic acid or carboxylic ester. Preferred heteroaryls are those having 5 or 6 atoms in the ring, such as indolyl, pyrrolyl, pyridinyl, pyrrazolyl, triazolyl, furanyl or thienyl.

The term "—($C_1$-$C_6$)-alkyl-heteroaryl" designates in the sense of the present invention an heteroaryl group, as defined above, linked to the rest of the molecule by an alkyl chain containing 1 to 6 carbon atoms. Advantageously, the "—($C_1$-$C_6$)-alkyl-heteroaryl" is a substituted or ($C_1$)-alkyl-heteroaryl.

In the sense of the present invention, the term "halogen" designates a fluorine, chlorine, bromine or iodine atom.

For the purpose of the invention, the term "pharmaceutically acceptable" is intended to mean what is useful to the preparation of a pharmaceutical composition, and what is generally safe and non-toxic, for a pharmaceutical use.

The term pharmaceutically acceptable salt, hydrate of solvate is intended to mean, in the framework of the present invention, a salt of a compound which is pharmaceutically acceptable, as defined above, and which possesses the pharmacological activity of the corresponding compound. Such salts comprise:

(1) hydrates and solvates,
(2) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and
(3) salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

DESCRIPTION DES FIGURES

FIG. 1 represents viability of HMLER CD24− cells (full line) and HMLER CD24+ cells (dotted line) at different concentration of salinomycine (1A), AM5 (16), AM9 (10) or AM13 (1D).

The Y axis represents cell viability and is expressed as percentage.

The X axis represents the concentration of each product in µM. The concentrations used are, from left to right from the intersection between the X and Y axes: 0.0001 µM; 0.001; 0.01 µM; 0.1 µM, 1 µM and 10 µM. Each dot on the line represents measured cell viability at the corresponding concentration.

FIG. 2 is a representative phase contrast photomicrographs of mammospheres formed after 11 days in the absence of any added compound (Control) or in the presence of a defined amount of salinomycine, AM5, AM9 or AM13. Sal analogues (AM5, AM13) reduced the number and the size of mammosphere at low nanomolar concentrations. The size of the mammospheres is correlated with progenitor cell proliferation, whereas the number of mammospheres formed after serial passages at clonal density is correlated with the self-renewal capacity of primitive Cancer Stem Cells. A smaller mass indicates cell death and regression of the mammosphere.

Figure 4:
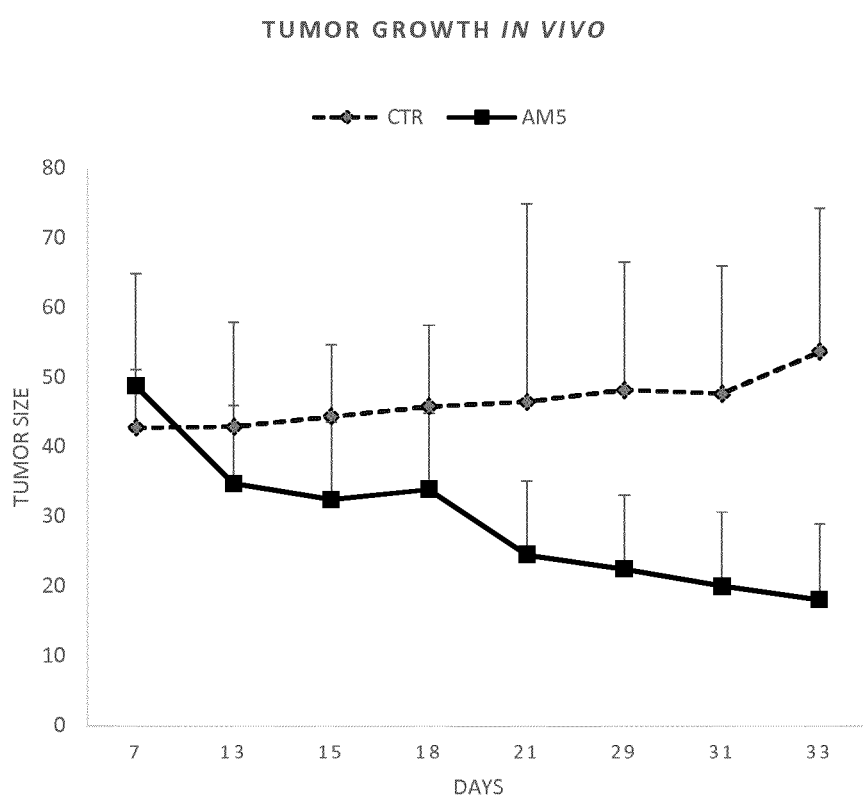

FIG. 4 represents MCF-7 tumor-growth curves of compound-treated mice (3 mg per kg body weight per day, intra peritoneal injection, n=5). Non-lethal injections of an active Sal analogue (AM5) inhibits breast cancer tumor growth in mice (n=5; error bars, s.e.m).

Figure 5:
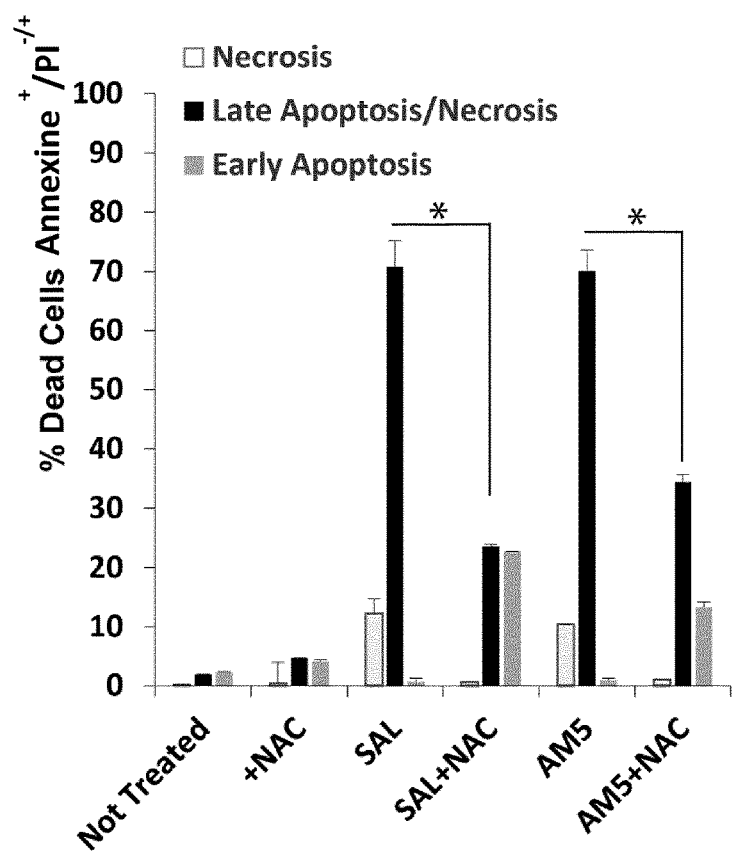

FIG. 5: Salinomycine analogue—induced cell death is inhibited by the ROS scavenger N-acetylcysteine (NAC). Cell lines were incubated with or without 500 nM of Sal analogues for 48 h. Apoptosis was evaluated by Annexin V-FITC and PI staining, and FACS analysis. All data are expressed as means±s.d. from three individual experiments (*; P<0.05)

Figure 6:
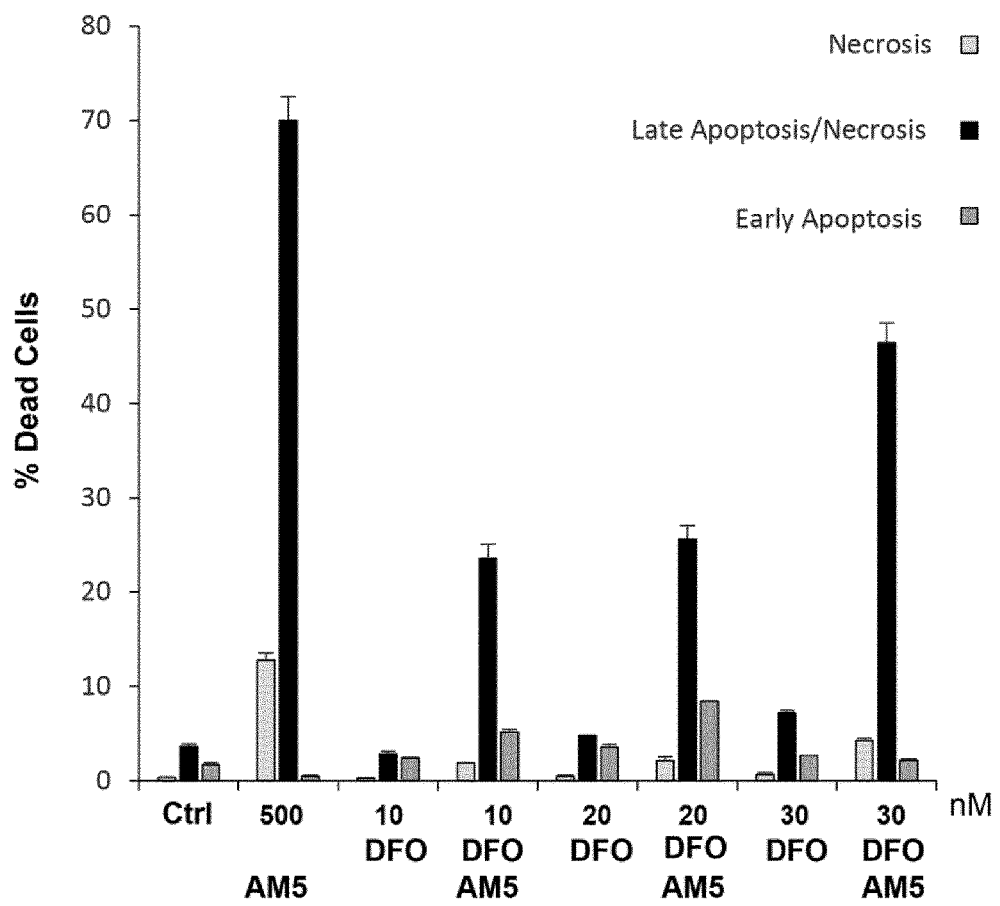

FIG. 6: Lysosomal iron mediates Sal analogues-activated cell death signaling. Sal analogue-induced cell death is inhibited by lysosomal iron chelator deferoxamine mesylate (DFO). Cells were treated as in (c) with or without the indicated concentration of DFO for 48 h. Apoptosis was evaluated as in c.

Figure 7:
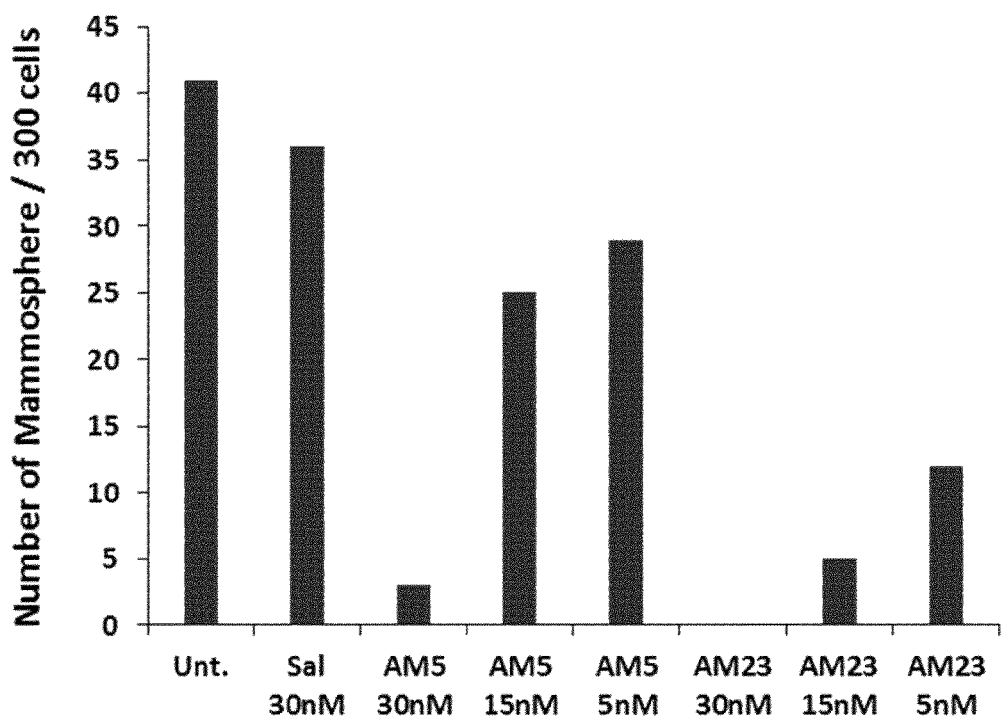
Figure 9:
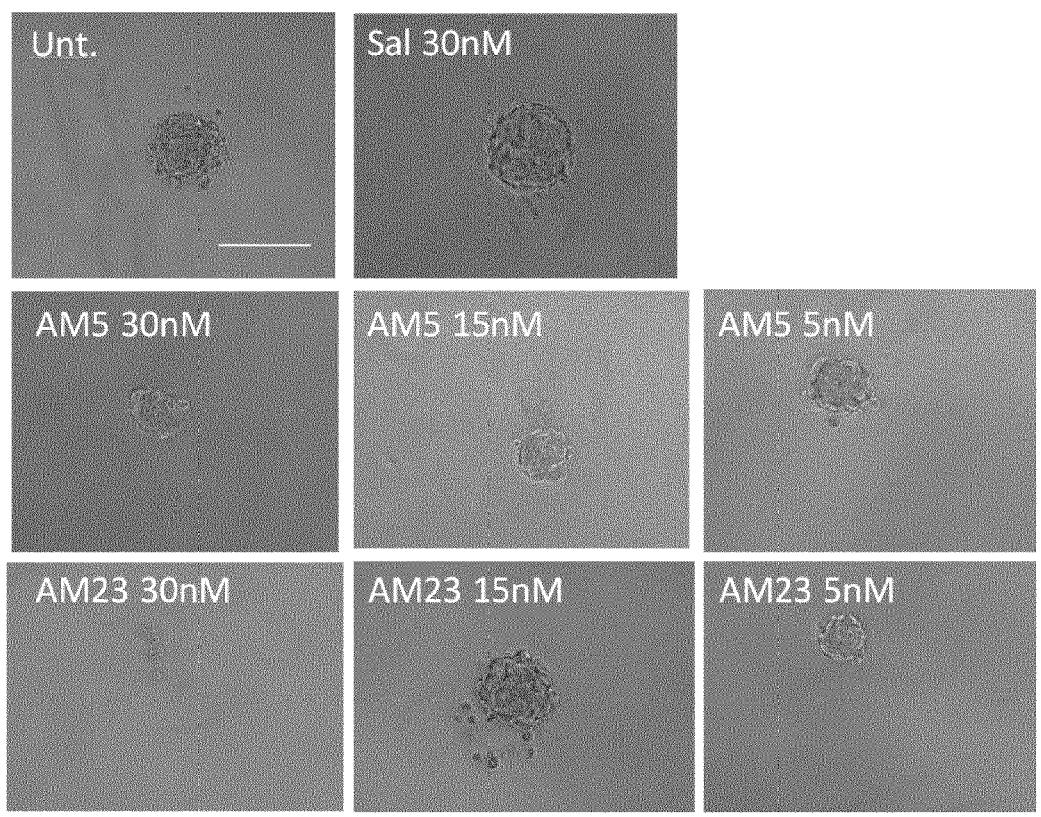

FIG. 7 represents the quantification of the number of mammospheres counted in experiments shown in FIG. 9. The number of mammospheres formed after serial passages at clonal density is correlated with the self-renewal capacity of primitive Cancer Stem Cells. A smaller mass indicates cell death and regression of the mammosphere. As compared to untreated cells or cells treated with salinomycine, only AM5 and more efficiently AM23 reduced the number of mammospheres.

Figure 8:
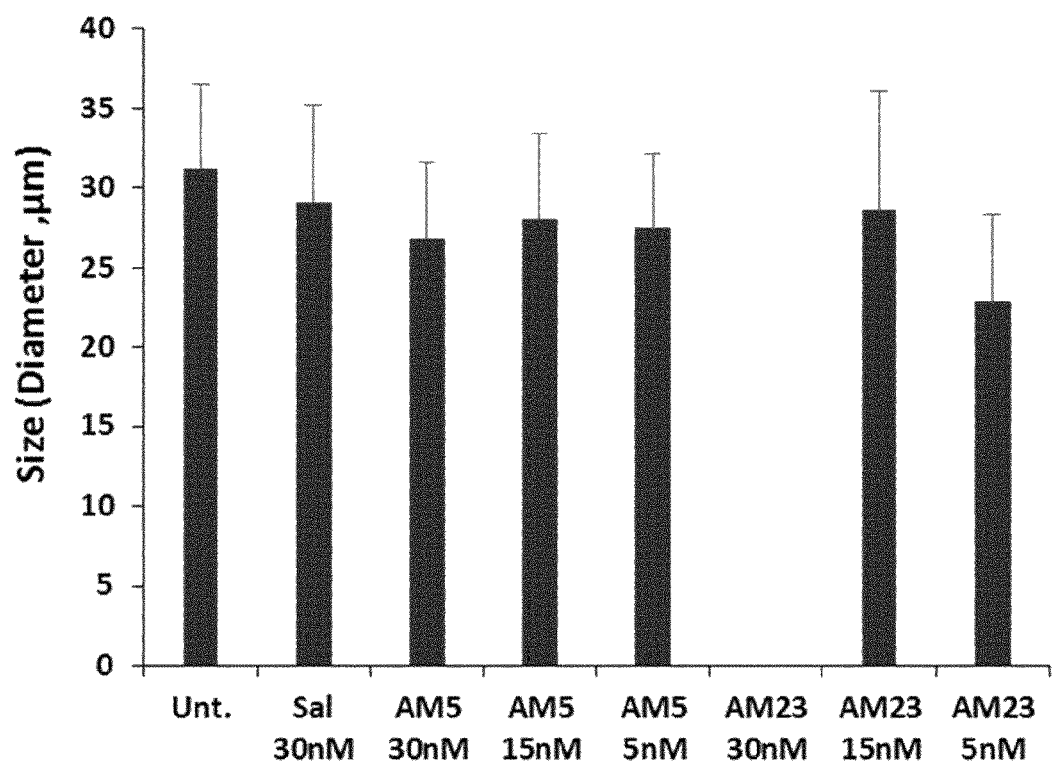

FIG. 8 represents the quantification of the size of mammospheres counted in experiments shown in FIG. 9. The size of the mammosphere is only reduced by the highest dose of AM23 whereas salinomycine, AM5 and lower dose of AM23 do not alter the tumor diameters.

FIG. 9 represents images of the third generation of mammospheres formed from individual HMLER CD24low cells treated during 7 days with the indicated drug. The size of the mammospheres is correlated with progenitor cell proliferation capacity, whereas the number of mammospheres formed after serial passages at clonal density is correlated with the self-renewal capacity of primitive Cancer Stem Cells. A smaller mass indicates cell death and regression of the mammosphere.

Figure 10:
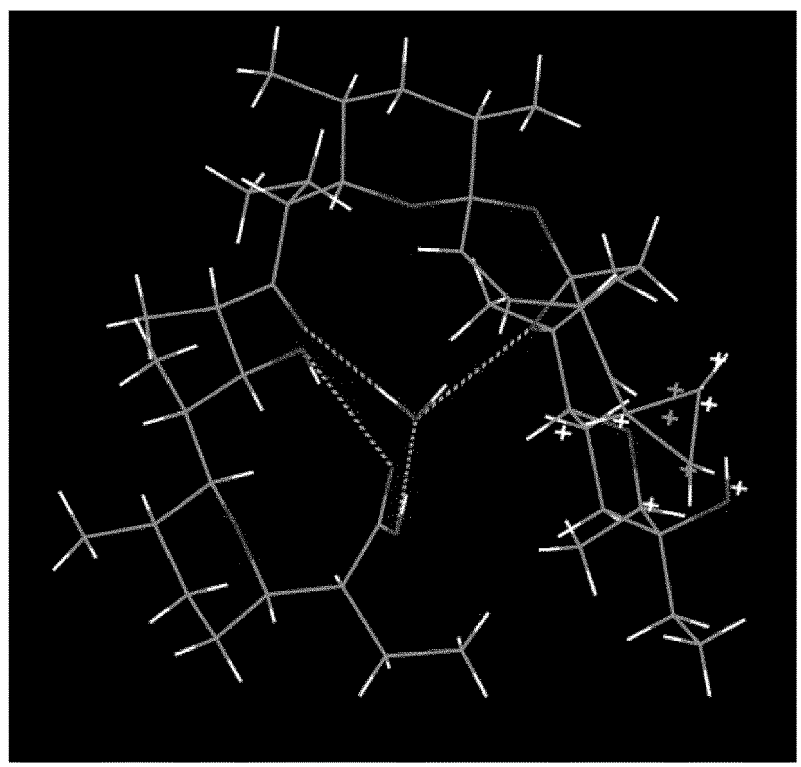
Figure 10:
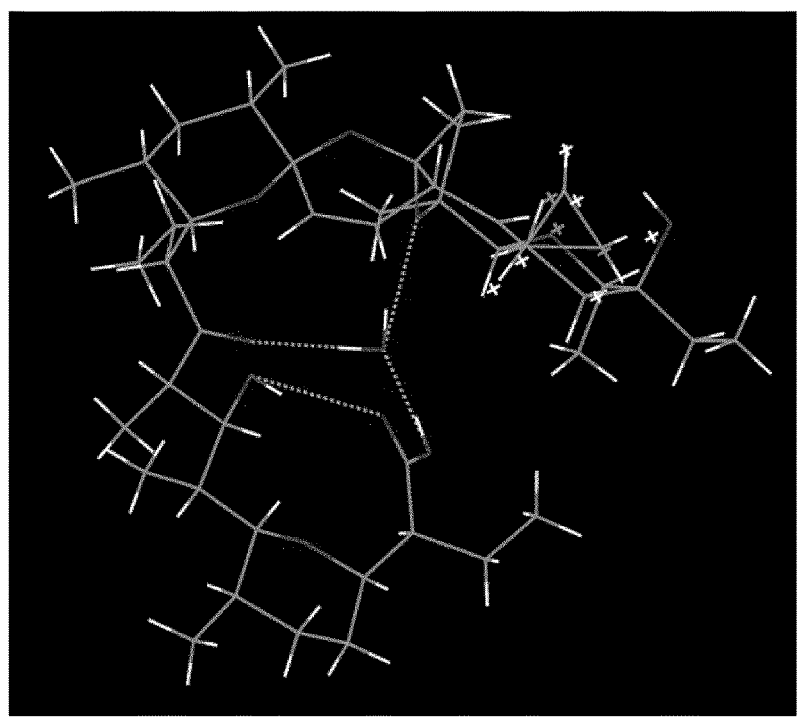

FIG. 10 is an ORTEP drawing of the X-Ray structure of AM23.

Figure 11:
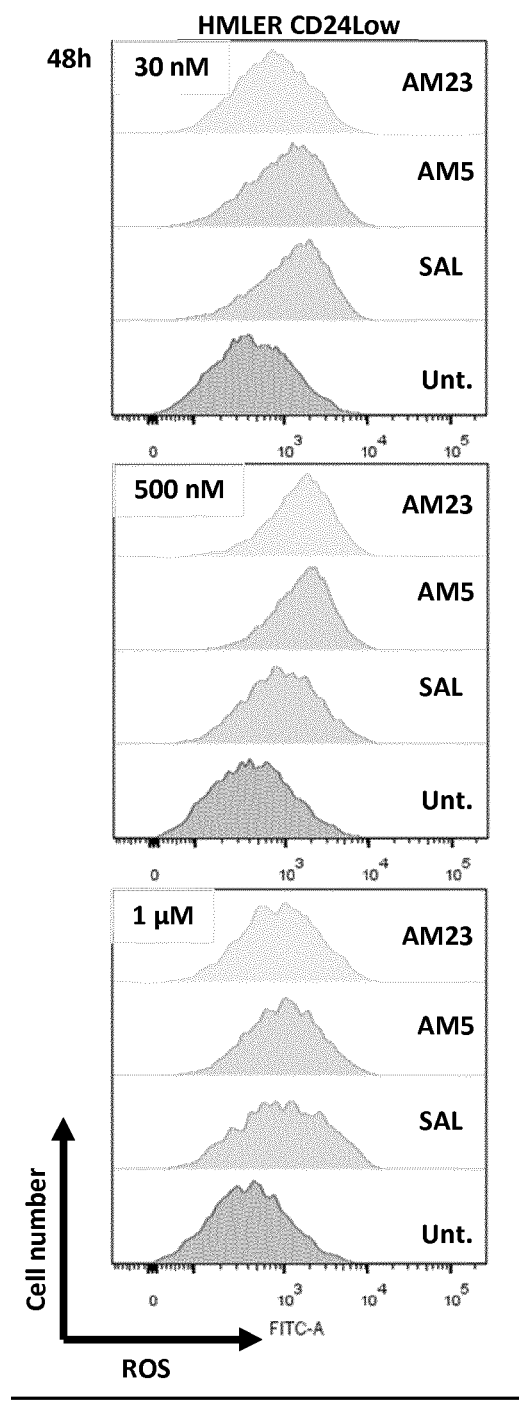

FIG. 11 represents FACS analyses of ROS in HMLER CD24low cells treated with salinomycine, AM5 and AM23.

Figure 12:
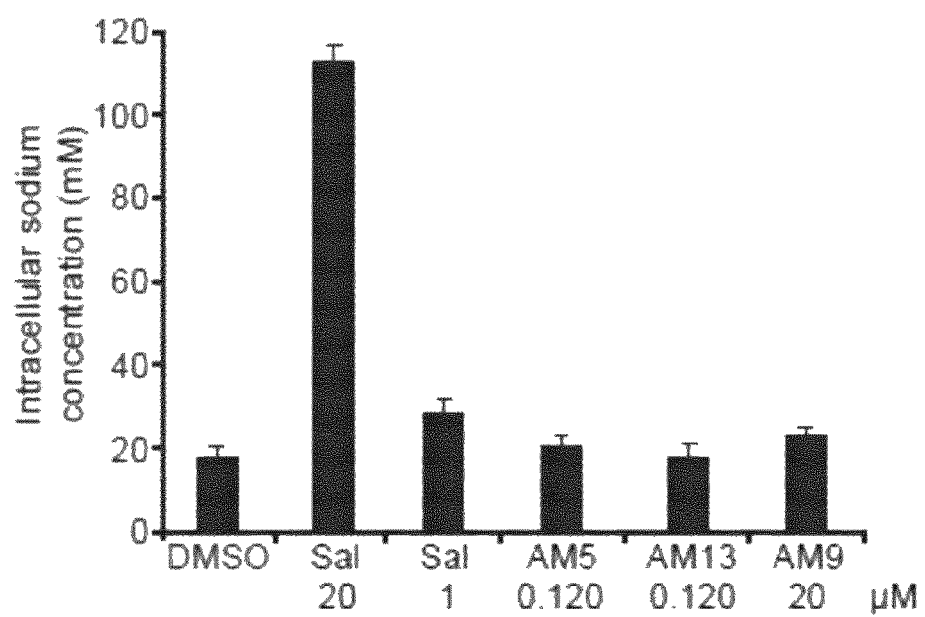
Figure 13:
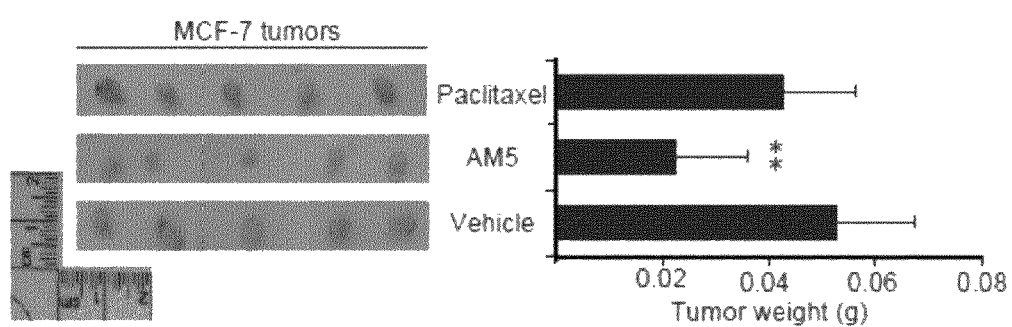

FIG. 12 is a graph representing the influence of salinomycine, AM5, AM13 and AM9 on intracellular sodium concentration FIG. 13 represents the evaluation of the prevention of tumor growth in MCF-7 xenograft-bearing mice.

Figure 14:
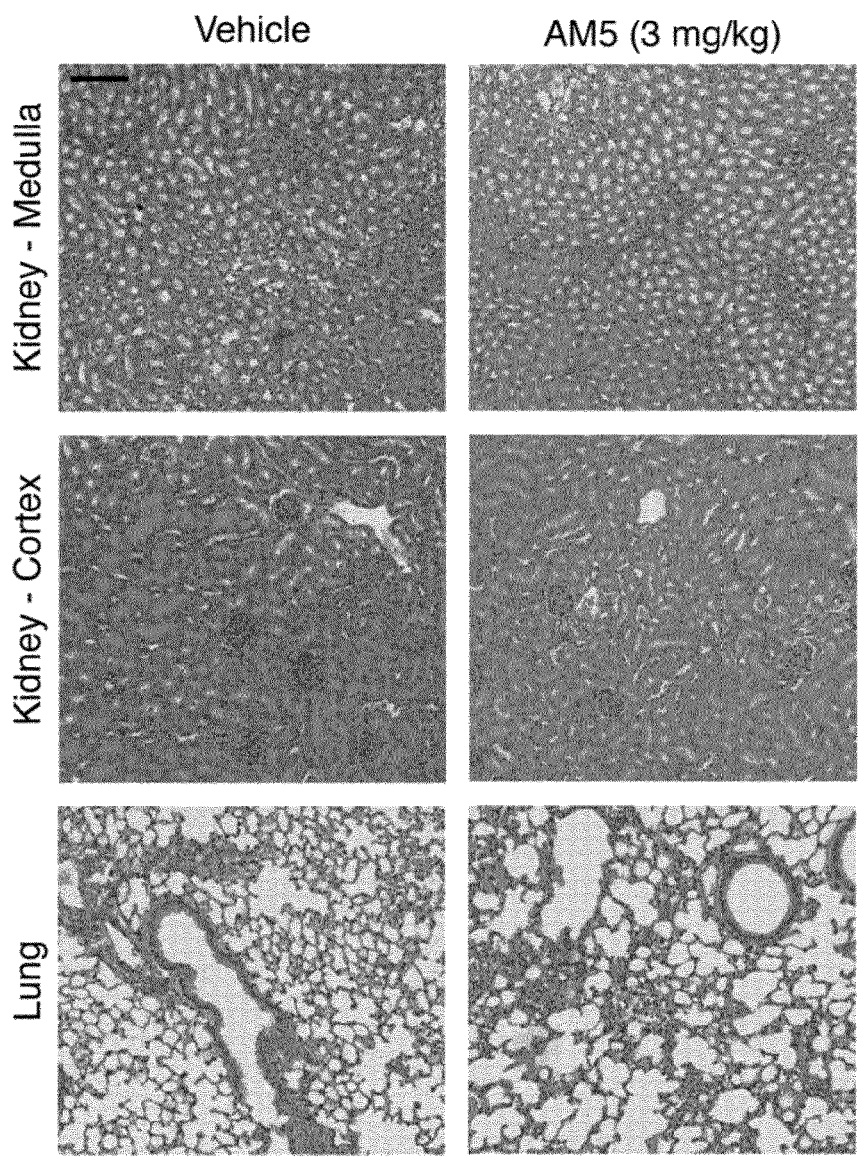

FIG. 14 represents a comparative H&E staining images of peripheral tissues of mice treated as in FIG. 13, representative of five biological replicates (scale bar, 100 μm).

Figure 15:
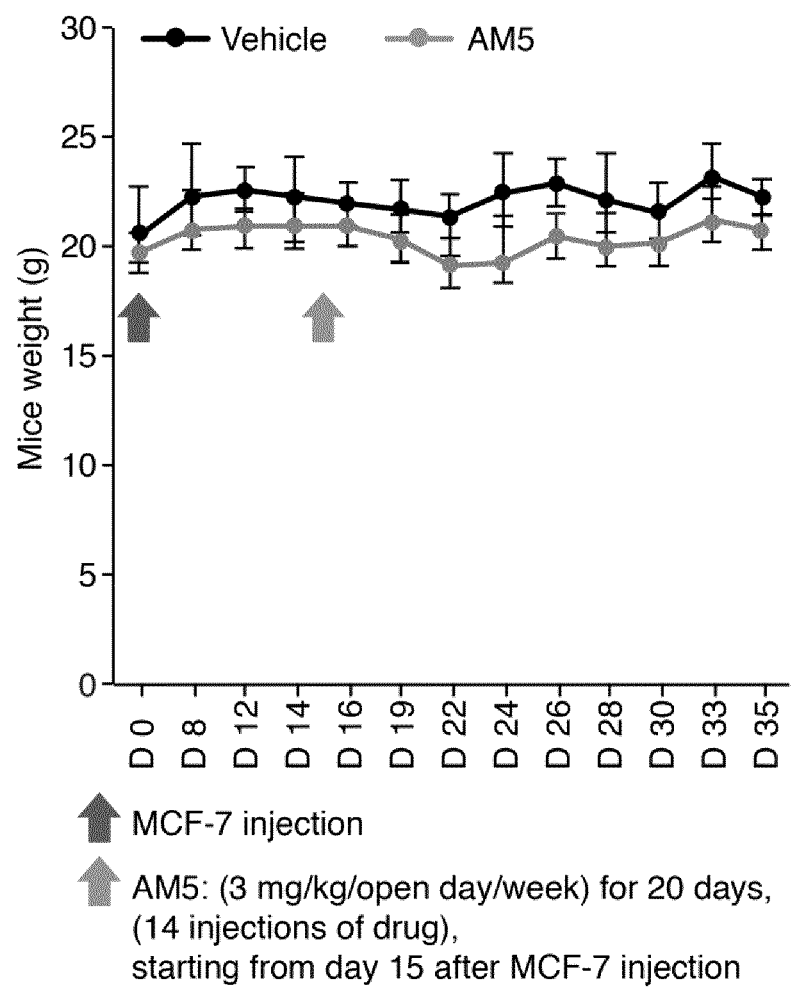

FIG. 15 is a graph representing the mice body-weight during treatment with AM5. Error bars for mice body weight represent s.d. and correspond to correspond to five animals per group.

Figure 16:
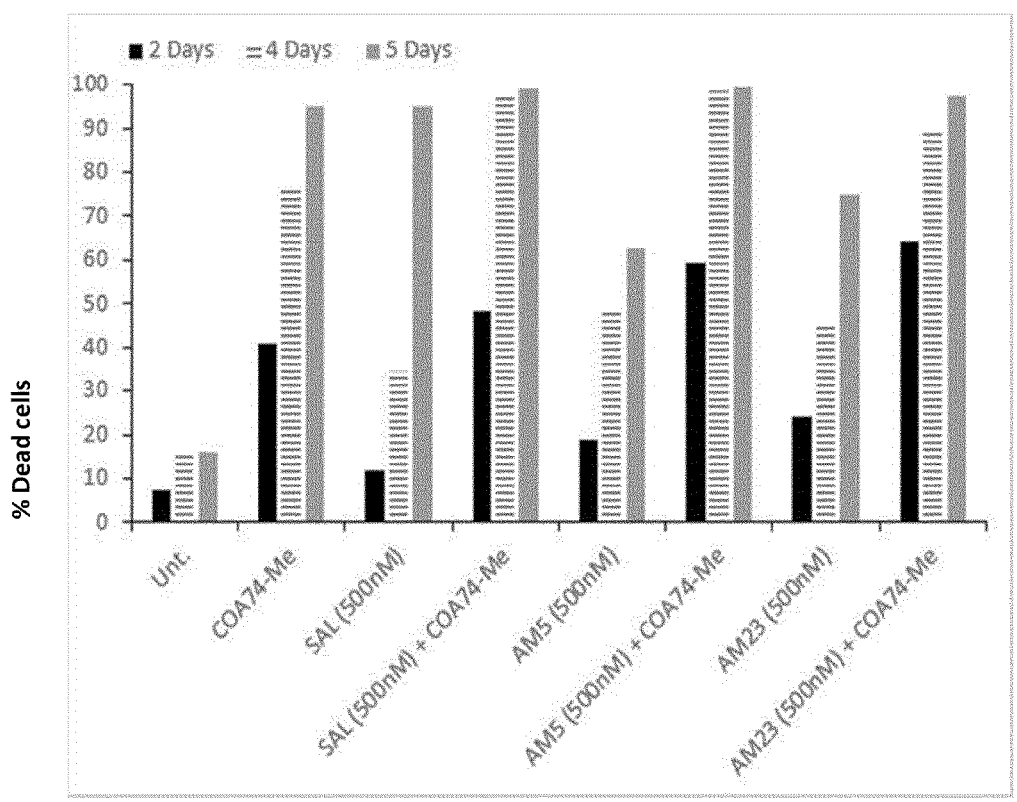

FIG. 16 is a graphic representation of percent of dead cells (DIOC6(3) negative/DAPI positive or negative)

Figure 17:
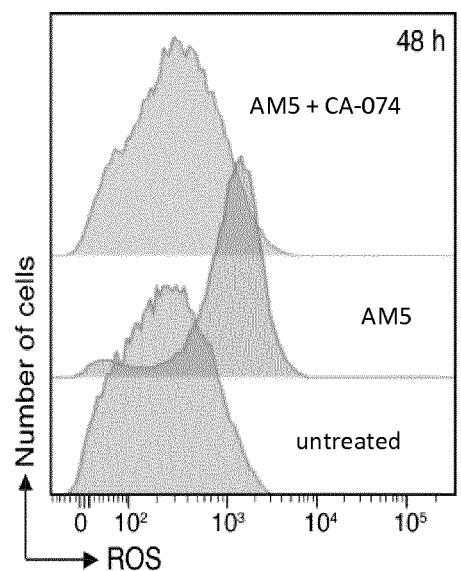

FIG. 17 represents a FACS analysis of ROS in cells treated for 48 h.

EXAMPLES

Example 1: Synthesis of Compound of Formula (I)

Preparation of Oxidized Salinomycin Acid (oxo-Sal-H) 2:

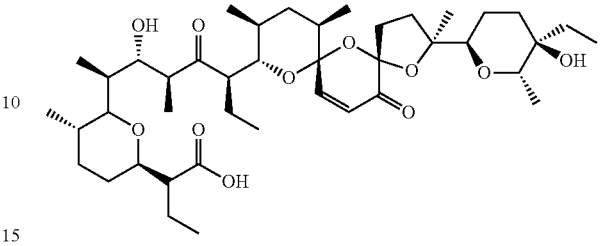

Salinomycin sodium (2.00 g, 2.587 mmol) was dissolved in 250 mL DCM and mangandioxide was added (9.00 g, 103.5 mmol, 40 eq). The suspension was stirred over night at room temperature. After complete conversion of starting material the mixture was filtrated on celite. The filtrate was extracted with 15 mM aqueous H2SO4 solution, dried on MgSO4 and concentrated to give product 2 (1.71 g, 2.28 mmol, 96%) as pure and white foam without any further purification.

1H NMR (CDCl3, 500 MHz, rt): 0.64-0.72 (6H, m), 0.72-0.82 (6H, m), 0.83-0.98 (12H, m), 1.04-1.17 (4H, m), 1.19-1.27 (2H, m), 1.30-1.57 (12H, m), 1.59-2.05 (14H, m), 2.43-2.60 (2H, m), 2.63-2.73 (1H, m) 2.76-2.88 (1H, m), 3.38-3.52 (1H, m), 3.66 (1H, d, J=9.6 Hz), 3.76 (1H, d, J=10.2 Hz), 3.88-4.04 (2H, m), 4.11-4.22 (1H, m), 6.20 (1H, d, J=10.7), 7.12 (1H, d, J=10.7).

13C NMR (CDCl3, 500 MHz, rt): 6.6, 7.0, 11.3, 12.1, 12.6, 13.1, 14.2, 15.5, 16.0, 17.6, 19.8, 20.7, 22.9, 26.4, 27.2, 28.3, 28.6, 32.1, 32.2, 33.2, 34.2, 35.5, 38.4, 40.2, 50.3, 51.6, 55.7, 67.7, 69.6, 71.0, 73.2, 75.8, 76.5, 76.7, 90.0, 98.0, 105.3, 107.1, 142.3, 183.2, 187.9, 217.9.

HRMS (ESI) m/z: Calculated for C42H68NaO11+[M+Na+] 771.4654, found: 771.4560.

Methylation of oxo-Sal-H to Form oxo-Sal-Me 3:

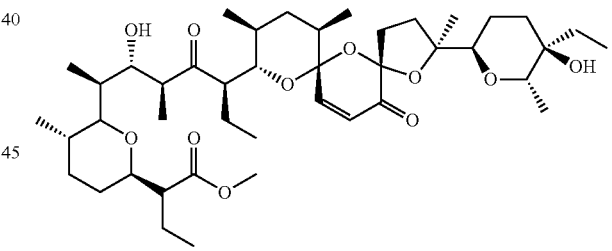

In a flame dried and Ar-flushed schlenk flask 2 (100 mg, 0.134 mmol) was introduced and dissolved in anhydrous DMF (3 mL). Cesium carbonate (56.5 mg, 0.174 mmol, 1.3 eq) was added followed by methyl iodide (11 μL, 0.174 mmol, 1.3 eq) and the solution was stirred for 24 h at room temperature. After completion of the reaction the solvent was removed, the residue was taken up in DCM and the solution was extracted with 15 mM aqueous H2SO4 solution, saturated NaHCO3 solution, water, brine and dried over MgSO4. The solution was filtered, concentrated and purified on silica gel with a CombiFlash using DCM/MeOH 10/0.2. The pure product 3 (96.5 mg, 0.126 mmol, 95%) was isolated as a white foam.

(The oxidation-methylation procedure can be inversed, the yields in both steps do not change so much.)

1H NMR (CDCl3, 300 MHz, rt): 0.63-0.72 (9H, m), 0.72-0.77 (3H, d, J=7.0 Hz), 0.80-0.89 (12H, m), 1.06-1.17 (7H, m), 1.17-1.21 (2H, m), 1.21-1.32 (3H, m), 1.32-1.46 (8H, m), 1.46-1.58 (3H, m), 1.60-1.80 (4H, m), 1.80-1.94

(2H, m), 1.98-2.12 (2H, m), 2.48-2.56 (1H, m), 2.58-2.68 (1H, m), 2.81-2.99 (2H, m), 3.26-3.32 (1H, m), 3.51 (1H, dd, J=9.8 Hz, 1.5 Hz), 3.59-3.73 (2H, m), 3.70 (3H, s, OMe), 3.85-3.97 (2H, m), 6.16 (1H, d, J=10.7 Hz), 7.18 (1H, d, 10.7 Hz).

13C NMR (CDCl3, 300 MHz, rt): 6.6, 7.2, 11.1, 11.9, 12.1, 14.0, 15.0, 17.9, 18.7, 19.8, 20.8, 22.6, 22.7, 26.3, 28.1, 29.2, 29.7, 30.3, 34.26, 34.30, 34.4, 36.6, 39.2, 39.9, 47.7, 49.1, 52.7, 57.5, 70.0, 71.2, 71.8, 72.3, 75.1, 77.1, 77.4, 88.7, 97.6, 105.5, 127.3, 144.2, 176.6, 190.9, 214.3.

HRMS (ESI) m/z: calculated for C43H70NaO11+ [M+Na+] 785.4810, found: 785.4807.

Procedure for Reductive Amination Reactions on 2 or 3:

100 mg of starting material 2 was dissolved in 3 ml MeOH, the primary amine was added (10 eq.), followed by AcOH (50 µL). The solution was stirred one hour at room temperature before CeCl3.7H2O was added. A solution of NaBH3CN (1.05-1.3 eq) in 2 mL of MeOH was added very slowly with the help of a syringe pump over a period of 8 h at room temperature. After further 4 h stirring at room temperature, a sample was taken out of the reaction mixture and a miniwork-up was done, followed by TLC. If starting material was not fully consumed, some more NaBH3CN in MeOH was slowly added until full conversion was visible. Then, a aqueous solution of 15 mM H2SO4 (2-4 mL) was carefully added, followed by DCM. The layers were separated and the aqueous layer was extracted 2 times with DCM. The combined organic layers were washed with aqueous 15 mM H2SO4, sat. aqueous NaHCO3 solution, water and brine. The solution was dried over MgSO4 and concentrated, before purification with a Combi Flash, using gradually 1 to 3% MeOH in DCM on silica gel. Most of side products could be removed by this step. For the final purification the product was purified by HPLC on C18-reversed phase column. Elution gradient: 50%/50% ACN/H2O (both with 0.1% formic acid) to 100% ACN within 12 min, 10-20 min 100% ACN (depending on polarity of products and side products). Amines eluted at around 60-90% ACN (AM5: 60%, AM9: 70%, AM13: 90-100%). Detection with UV detector at a wavelength of 217 nm.

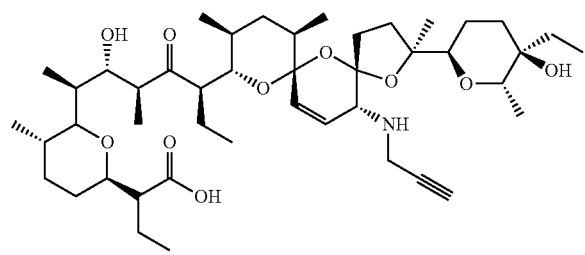 [SMILES: C#CCN[C@@H]1C=C[C@]2(O[C@H]([C@@H](CC)C(=O)[C@@H](C)[C@@H](O)[C@H](C)C3O[C@@H](C(CC)C(=O)O)CC[C@@H]3C)[C@@H](C)C[C@H]2C)O[C@@]12CC[C@@](C)([C@H]1CC[C@](O)(CC)[C@H](C)O1)O2]

Preparation of AM5

Sal-Propargylamine was prepared using 103 mg of 2 (0.134 mmol), 86 µL (1.34 mmol, 10 eq) propargyl amine, 11 mg (0.174 mmol, 1.3 eq) NaBH3CN, 50.0 mg (0.134 mmol, 1 eq) of CeCl3.7H2O and 50 µL acetic acid in 8 mL of MeOH. After purification with CombiFlash and HPLC 25 mg (0.032 mmol, 24%) of pure product could be isolated as colorless foam.

1H NMR (CDCl3, 600 MHz, 5° C.): 0.66 (3H, d, J=7.2 Hz, C39H3), 0.71 (3H, d, J=6.6 Hz, C34H3), 0.75 (3H, dd, J=J=7.8 Hz, C37H3), 0.77 (3H, d, J=7.2 Hz, C38H3), 0.85 (3H, d, J=6.6 Hz, C35H3), 0.86 (3H, m, C32H3), 0.88 (3H, m, C40H3), 0.90 (3H, m, C42H3), 1.13 (1H, dd, J=J=13.8 Hz, C15H), 1.21 (3H, d, J=7.2 Hz, C30H3), 1.25-1.38 (8H, m, C41H, C31H2, C36H, C33H3, C4H), 1.39-1.48 (3H, m, C5H, C8H, C41H), 1.49-1.55 (1H, m, C26H), 1.55-1.63 (3H, m, C26H, C27H2), 1.63-1.71 (3H, m, C14H, C15H, C16H), 1.71-1.80 (3H, m, C6H, C23H, C5H), 1.80-1.91 (2H, m, C36H, C4H), 1.91-2.00 (2H, C22H2), 2.09-2.16 (1H, m, C23H), 2.36-2.40 (1H, s, ≡CH), 2.55-2.64 (2H, m, C12H, C10H), 2.84-2.91 (1H, dt, C2H), 3.53 (1H, m, C13H), 3.57-3.63 (2H, C25H, m, C7H), 3.81-3.85 (1H, m, C29H), 3.91-4.01 (2H, m, C3H, C20H), 4.15 (1H, d, J=10.2 Hz, C9H), 4.28 (2H, bs, NHCH2), 6.28 (1H, m, C19H), 6.44 (1H, d, J=9.6 Hz, C18H).

13C NMR (CDCl3, 600 MHz, 5° C.): 6.5 (C32), 7.1 (C39), 11.2 (C40), 12.2 (C38), 12.5 (C42), 13.3 (C37), 14.5 (C30), 15.6 (C34), 16.7 (C36), 17.6 (C35), 20.0 (C4), 21.8 (C26), 22.9 (C41), 25.0 (C33), 26.4 (C5), 28.1 (C6), 28.8 (C27), 30.7 (C31), 30.8 (C23), 32.3 (C14), 36.1 (C8), 37.1 (NHCH2), 37.6 (C15), 39.0 (C16), 40.0 (C22), 49.2 (C2), 50.0 (C10), 53.0 (C20), 55.2 (C12), 68.9 (C9), 71.1 (C28), 71.5 (C7), 72.9 (C25), 75.5 (C3), 75.8 (C13), 76.3 (≡CH), 76.9 (C29), 77.3 (≡C—), 88.6 (C24), 98.6 (C17), 105.6 (C21), 125.8 (C19), 132.2 (C18), 180.8 (C1), 216.1 (C11).

HRMS (ESI) m/z: Calculated for C45H74NO10+ [M+H+] 788.5307, found: 788.5304.

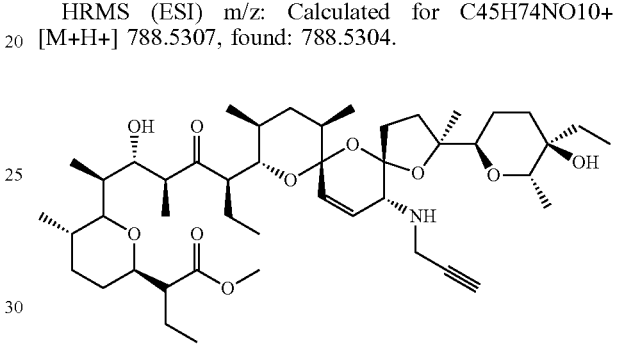

Preparation of AM9

Me-Sal-propargylamine was prepared using 106 mg of 3 (0.139 mmol), 89 µL (1.39 mmol, 10 eq) propargyl amine, 9.6 mg (0.153 mmol, 1.1 eq) NaBH3CN, 51.8 mg (0.138 mmol, 1 eq) of CeCl3.7H2O and 50 µL acetic acid in 8 mL of MeOH. After purification with CombiFlash and HPLC 25 mg (0.031 mmol, 22%) of pure product could be isolated as colorless foam.

1H NMR (CDCl3, 500 MHz, 5° C.): 0.72 (3H, d, J=6.9 Hz), 0.75-0.87 (11H, m), 0.88-0.99 (9H, m), 1.07 (1H, ddd, J=13.1 Hz, 13.1 Hz, 12.1 Hz), 1.20-1.68 (21H, m), 1.70-2.05 (8 Hz, m), 2.10-2.26 (3H, m), 2.30-2.41 (2H, m), 2.69-2.74 (1H, m), 3.04 (1H, dt, J=10.8 Hz, 4.1 Hz), 3.47-3.72 (4H, m), 3.80-3.88 (1H, m), 3.90 (3H, s), 4.02-4.09 (2H, m), 6.01-6.08 (2H, m).

13C NMR (500 MHz, CDCl3, 5° C.): 6.5, 7.4, 11.0, 12.0, 13.2, 13.9, 14.7, 15.7, 17.5, 19.7, 22.2, 22.7, 25.5, 26.2, 28.0, 29.0, 30.6, 30.7, 32.9, 36.4, 37.1 (2C), 38.6, 38.7, 40.3, 48.0, 48.6, 52.6, 55.2, 56.6, 69.2, 71.0, 71.7, 73.9, 75.1, 76.9, 77.3, 80.1, 88.0, 98.6, 102.0, 108.3, 123.2, 130.5, 176.2, 214.0.

HRMS (ESI) m/z: calculated for C46H76NO10+ [M+H+] 802.5464, found: 802.5465.

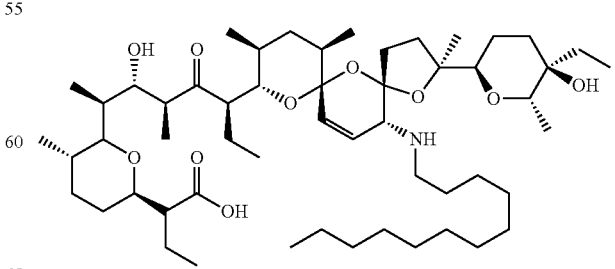

Preparation of AM13

Sal-Dodecylamine was prepared using 103 mg of 2 (0.138 mmol), 255.8 mg (1.38 mmol, 10 eq) dodecyl amine, 9 mg (0.145 mmol, 1.05 eq) NaBH3CN, 51.4 mg (0.138 mmol, 1 eq) of CeCl3.7H2O and 20 μL acetic acid in 8 mL of MeOH. After purification with CombiFlash and HPLC 14 mg (0.0152 mmol, 11%) of pure product could be isolated as colorless foam.

1H NMR (CDCl3, 500 MHz, 5° C.): 0.67 (3H, d, J=6.9 Hz), 0.66-0.77 (9H, m), 0.78-0.90 (15H, m), 1.10-1.51 (34H, m), 1.51-1.78 (9H, m), 1.80-2.10 (6H, m), 2.50-2.60 (2H, m), 2.77-2.87 (1H, m), 3.30-3.62 (5H, m), 3.68-3.80 (2H, m), 3.97-4.04 (1H, m), 4.20-4.30 (1H, m), 6.32-6.42 (2H, m).

13C NMR (500 MHz, CDCl3, 5° C.): 6.5, 7.1, 11.3, 12.3, 12.8, 13.1, 14.3, 14.4, 15.5, 16.5, 17.6, 20.3, 21.8, 22.81, 22.84, 24.5, 26.4, 26.7, 27.3, 28.2, 29.0, 29.5, 29.6, 29.76, 29.81 (4C), 30.5, 31.0, 32.0, 32.2, 35.8, 37.7, 39.0, 40.6, 48.6, 49.3, 50.5, 55.0, 55.1, 71.05, 71.14, 73.0, 75.5, 76.4, 77.0, 88.8, 99.0, 106.5, 128.0, 130.9, 204.7, 214.8.

HRMS (ESI) m/z: calculated for $C_{54}H_{96}NO_{10}^+$ [M+H+] 918.7029, found: 918.7034.

Sal-cyclopropylamine was prepared using 100 mg of 2 (0.133 mmol), 94 μL (1.33 mmol, 10 eq) cyclopropyl amine, 11 mg (0.17 mmol, 1.3 eq) NaBH3CN, 50.0 mg (0.134 mmol, 1 eq) of CeCl3.7H2O and 50 μL acetic acid. AM23 was obtained as a colorless foam (44 mg, 42%).

1H NMR (CDCl3, 500 MHz, 278 K) δ 0.47-0.58 (2H, m), 0.69 (3H, J=10.0 Hz), 0.71-0.78 (9H, m), 0.78-0.95 (14H, m), 1.12-1.50 (16H, m), 1.50-1.75 (5H, m), 1.76-1.91 (4H, m), 2.02-2.20 (2H, m), 2.60 (1H, d, J=10.5 Hz), 2.62-2.68 (1H, m), 2.70-2.78 (1H, m), 2.78-2.88 (1H, m), 3.37 (1H, s), 3.53-3.80 (3H, m), 3.82-3.89 (1H, m), 4.08 (1H, d, J=9.5 Hz), 5.15 (2H, br s), 6.13 (2H, s).

$^{13}$C NMR (CD3CN, 125 MHz, 278 K) δ 5.9, 6.4, 6.9, 7.7, 12.0, 12.4, 13.6, 13.7, 15.2, 16.1, 17.4, 17.9, 21.0, 22.7, 24.0, 25.7, 27.3, 29.1, 30.1, 31.8, 31.9, 33.4, 36.8, 39.0, 39.5, 41.2, 49.0, 50.4, 56.7, 57.6, 69.5, 71.5, 72.4, 74.7, 76.0, 77.1, 77.9, 89.7, 99.9, 107.9, 126.0, 130.8, 178.8, 214.7.

HRMS (ESI) m/z: calculated for $C_{45}H_{75}NO_{10}^+$ [M+H$^+$] 789.5385, found: 789.5381. FIG. 10 shows the 3D-structure of compound AM23 which confirms unambiguously the crystalline structure and the stereochemistry of AM23.

Example 2: IC$_{50}$ Assessment

Cell viability assay was carried out by plating 1000 cells per well in 96-well plates. NAC (2 mM, A9165 Sigma) or DFO (1 mM) were pretreated 2 hours prior to the compound treatment. CellTiter-Blue® Reagent (Promega; G3582) (20 μl/well) was added after 24, 48, or 72 hours treatment and cells were incubated for 1 hour before recording fluorescence (560(20)Ex/590(10)Em) using a Perkin Elmer Wallac 1420 Victor2 Microplate Reader.

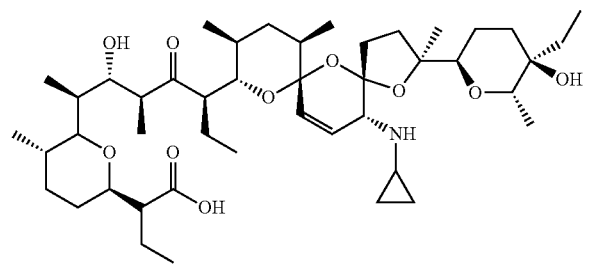

Preparation of AM23

| Compound ID | Compound | CD24− | CD24+ |
|---|---|---|---|
| Salinomycine | | 1.56 | 10.97 |
| AM6 | | 6.18 | 12.77 |

-continued

| Compound ID | Compound | CD24− | CD24+ |
|---|---|---|---|
| AM7 | | 7.25 | 12.52 |
| AM5 | | 0.0849 | 3.5147 |
| AM9 | | 11.756 | 22 |
| AM10 | | 10.012 | 19.74 |
| AM8 | | 1.02 | 8.06 |

-continued

| Results: | | | |
|---|---|---|---|
| Compound ID | Compound | CD24− | CD24+ |
| AM11 | | 0.8 | 6.7 |
| AM12 | | 1.79 | 6.92 |
| AM13 | | 0.0727 | 3.191528 |
| AM16 | | 0.30 | 1.17 |
| AM17 | | 0.1 | 2 |

-continued
| Compound ID | Compound | CD24− | CD24+ |
|---|---|---|---|
| AM18 | 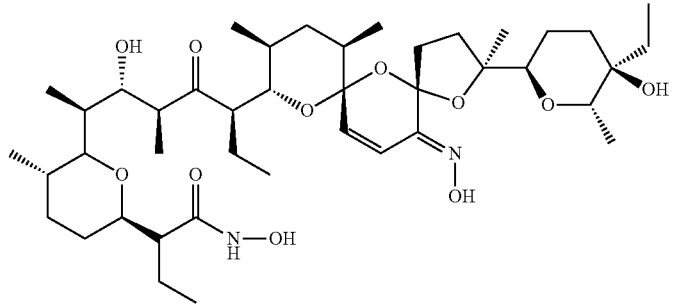 [SMILES: CCC(C(=O)NO)[C@H]1CC[C@H](C)C([C@@H](C)[C@H](O)[C@H](C)C(=O)[C@H](CC)[C@H]2O[C@]3(C=C/C(=N\O)[C@]4(CC[C@@](C)([C@H]5CC[C@](O)(CC)[C@H](C)O5)O4)O3)[C@H](C)C[C@@H]2C)O1] | 0.1 | 2.5 |
| AM21 | 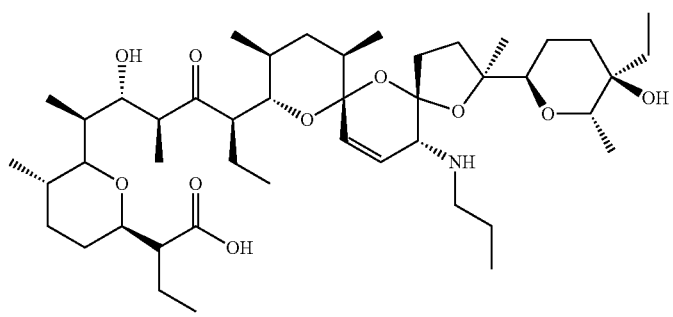 [SMILES: CCCN[C@@H]1C=C[C@]2(O[C@H]([C@@H](CC)C(=O)[C@@H](C)[C@@H](O)[C@H](C)C3O[C@@H](C(CC)C(=O)O)CC[C@@H]3C)[C@@H](C)C[C@H]2C)O[C@@]12CC[C@@](C)([C@H]1CC[C@](O)(CC)[C@H](C)O1)O2] | 0.34 | 6.50 |
| AM22 | 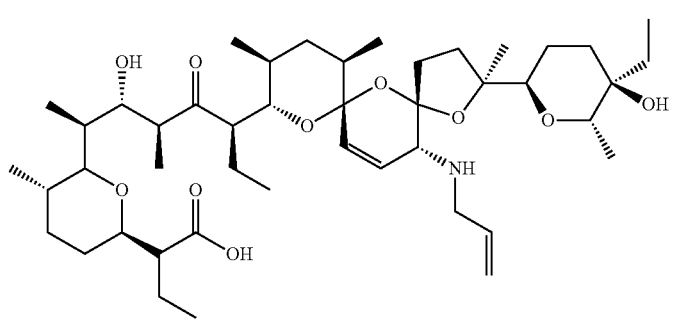 [SMILES: C=CCN[C@@H]1C=C[C@]2(O[C@H]([C@@H](CC)C(=O)[C@@H](C)[C@@H](O)[C@H](C)C3O[C@@H](C(CC)C(=O)O)CC[C@@H]3C)[C@@H](C)C[C@H]2C)O[C@@]12CC[C@@](C)([C@H]1CC[C@](O)(CC)[C@H](C)O1)O2] | 0.30 | 1.53 |
| AM23 | 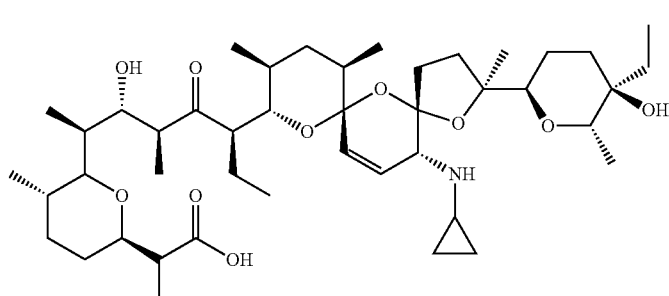 | 0.043 | 1.20 |

-continued
| Compound ID | Compound | CD24− | CD24+ |
|---|---|---|---|
| AM24 | 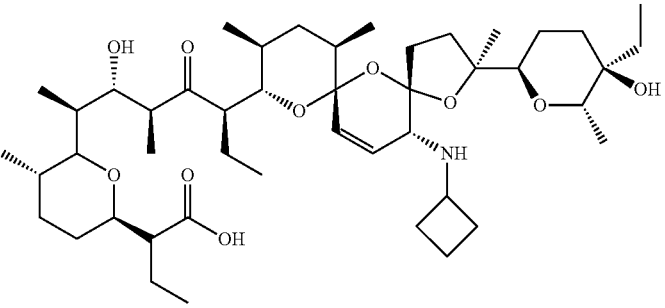 [SMILES: CCC(C(=O)O)[C@H]1CC[C@H](C)C([C@@H](C)[C@H](O)[C@H](C)C(=O)[C@H](CC)[C@H]2O[C@]3(C=C[C@@H](NC4CCC4)[C@]4(CC[C@@](C)([C@H]5CC[C@](O)(CC)[C@H](C)O5)O4)O3)[C@H](C)C[C@@H]2C)O1] | 0.107 | 1.40 |
| AM25 | 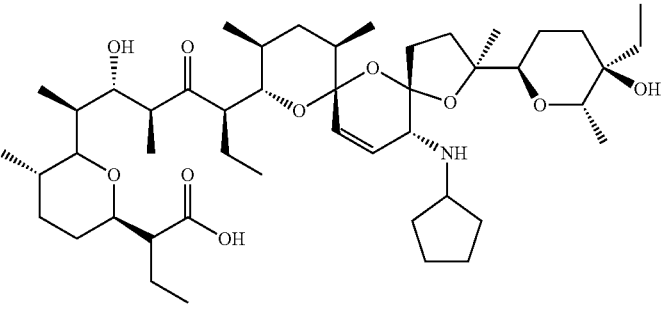 [SMILES: CCC(C(=O)O)[C@H]1CC[C@H](C)C([C@@H](C)[C@H](O)[C@H](C)C(=O)[C@H](CC)[C@H]2O[C@]3(C=C[C@@H](NC4CCCC4)[C@]4(CC[C@@](C)([C@H]5CC[C@](O)(CC)[C@H](C)O5)O4)O3)[C@H](C)C[C@@H]2C)O1] | 0.108 | 1.36 |
| AM26 | 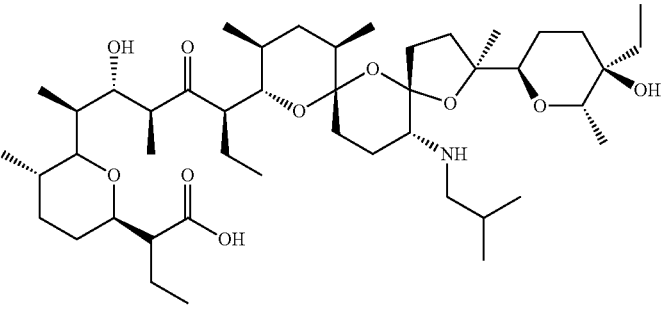 [SMILES: CCC(C(=O)O)[C@H]1CC[C@H](C)C([C@@H](C)[C@H](O)[C@H](C)C(=O)[C@H](CC)[C@H]2O[C@]3(CC[C@@H](NCC(C)C)[C@]4(CC[C@@](C)([C@H]5CC[C@](O)(CC)[C@H](C)O5)O4)O3)[C@H](C)C[C@@H]2C)O1] | 1.149 | 10.09 |
| AM28 | 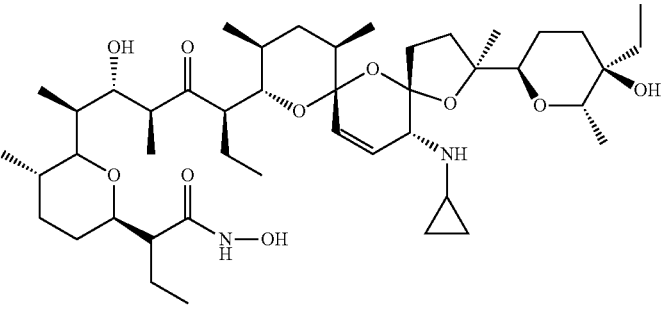 [SMILES: CCC(C(=O)NO)[C@H]1CC[C@H](C)C([C@@H](C)[C@H](O)[C@H](C)C(=O)[C@H](CC)[C@H]2O[C@]3(C=C[C@@H](NC4CC4)[C@]4(CC[C@@](C)([C@H]5CC[C@](O)(CC)[C@H](C)O5)O4)O3)[C@H](C)C[C@@H]2C)O1] | 6.43 | 5.83 |

The above results show that the compounds not containing an amine functionality at the 20-position have lower potency than salinomycine against cancer stem cells.

Introducing an amine function at position 20 of salinomycine results in a significantly improved activity against CD24 cells (AM 5, AMB, AM11, AM12, AM13 and AM23), up to an 18 fold improvement.

Replacement of the carboxylic acid functionality in the 1-position of salinomycine with an ester group results in compounds with lower efficiency than salinomycine (AM9 and AM10).

These results demonstrate that both the amine and a functional group capable of chelating iron, such as a carboxylic acid are necessary for improved activity. It is contemplated that the presence of these two functional groups help iron coordination, thereby favoring the Fenton reaction in the lysosomes.

The compounds of formula (I) are therefore useful for the treatment of cancer and/or the prevention of cancer relapse and/or metastases.

Example 3: Effect of AM5, AM9 and AM13 on the Proliferation of HMLER CD24– Cells AM5, AM9, AM13 and salinomycine were assessed for their capability to inhibit cell proliferation and formation of mammospheres.

Figure 1:
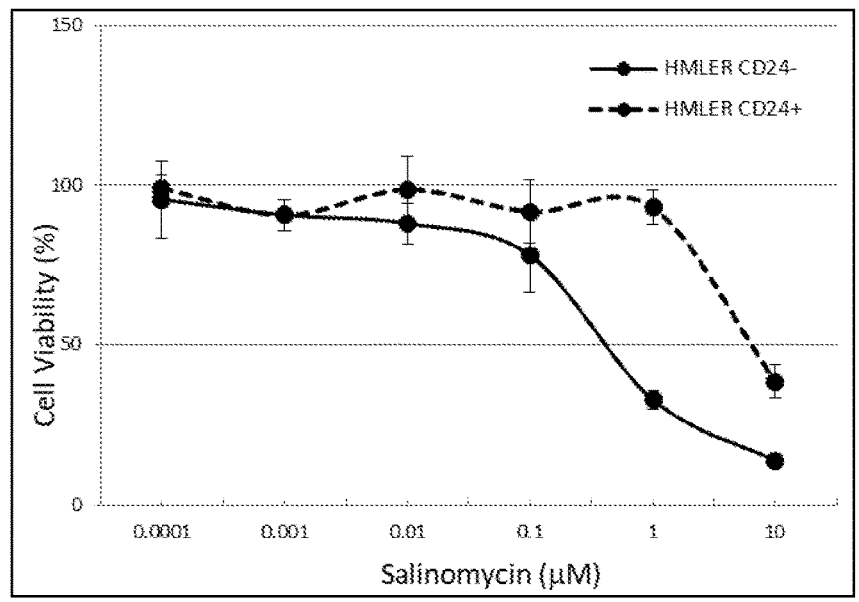
Figure 1:
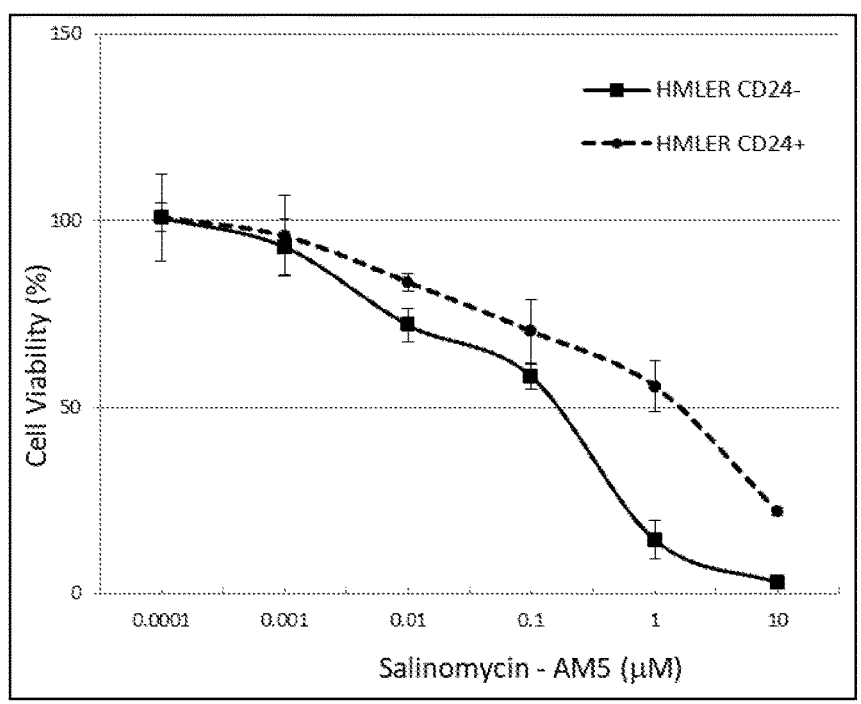
Figure 1:
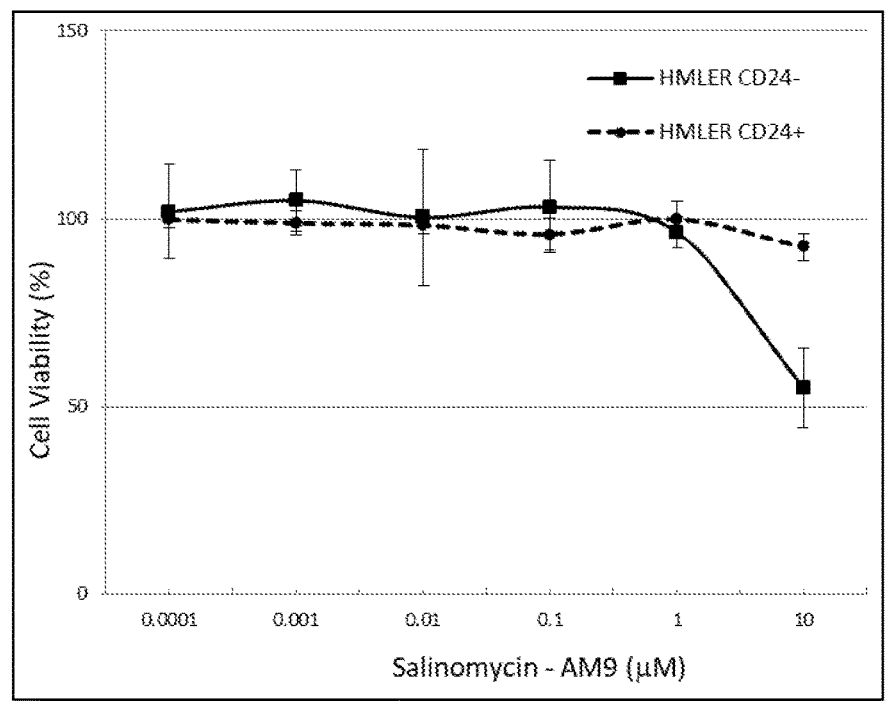
Figure 1:
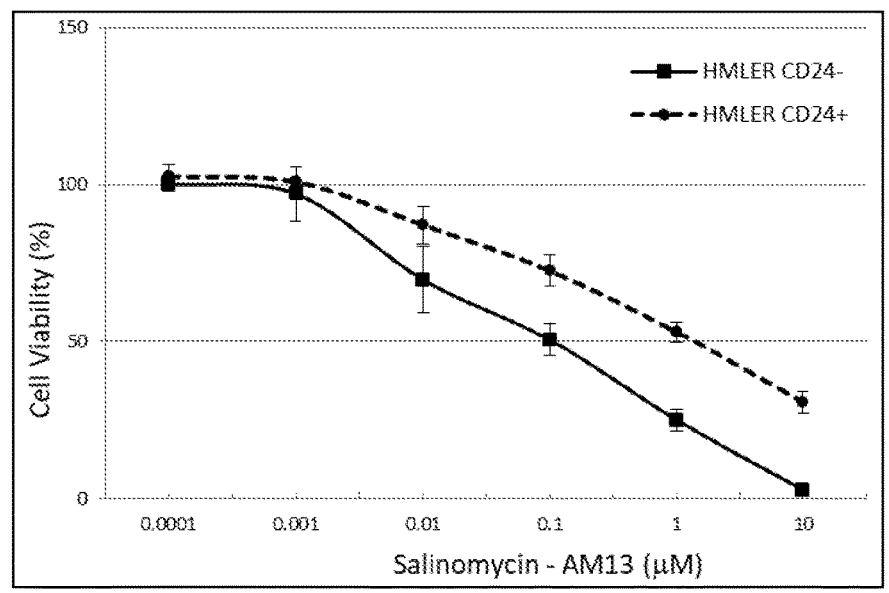
Figure 2:
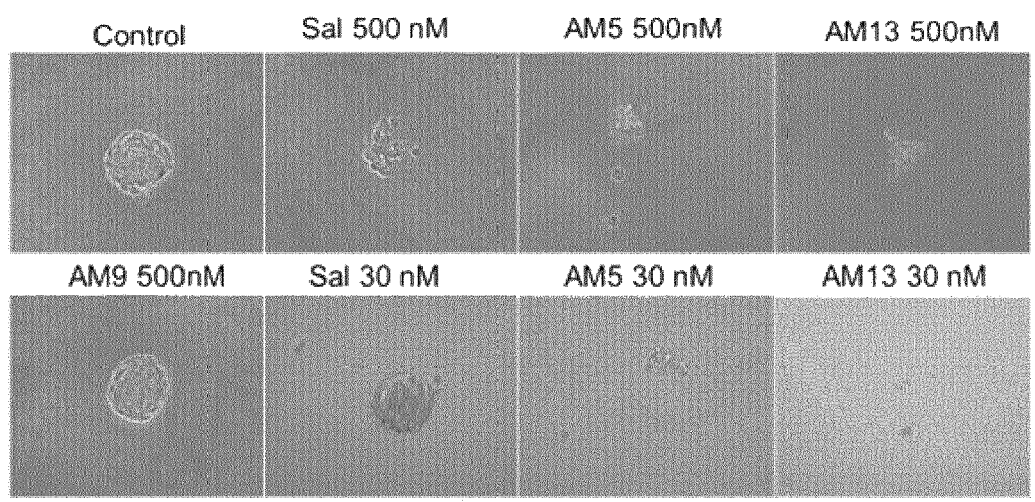

The results are presented in FIG. 2.

At 30 nM, AM 5 and AM13 inhibit cell proliferation with a ten-fold improved efficacy in comparison with salinomycine.

In contrast, AM 9 did not inhibit cell proliferation, even at 500 nM.

These results thus indicate that the compounds of formula (I) according to the present invention are capable of inhibiting the formation of mammospheres more efficiently than salinomycine.

Example 4: Effect of AM5, Taxol and Combination Thereof on the Proliferation of HMLER CD24– Cells AM5, Taxol and a combination of AM5 and Taxol were also assessed for their capability to inhibit cell proliferation and formation of mammospheres.

Figure 3:
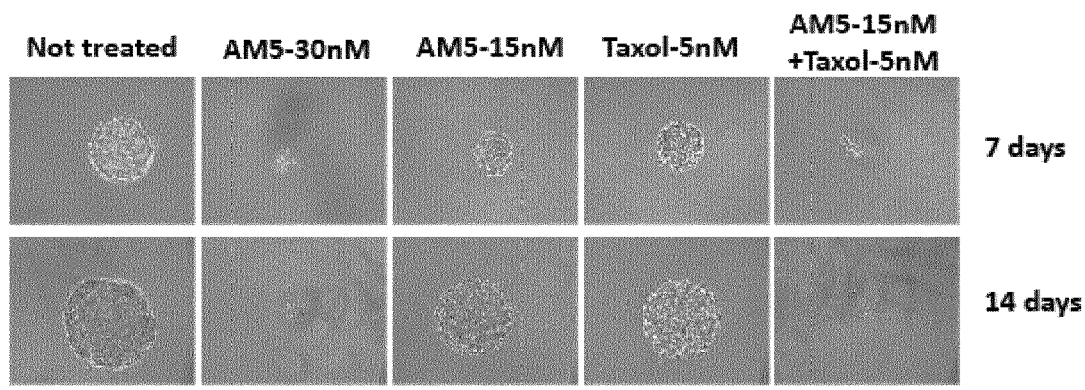
FIG. 3A is a representative phase contrast photomicrographs of mammospheres formed after 7 or 14 days in the absence of any added compound (Not treated) or in the presence of a defined amount of salinomycine, AM5, Taxol or the combination of AM5 and Taxol. A smaller mass indicates cell death and regression of the mammosphere.
FIG. 3B represents the quantification of the number and the size of mammosphere. The combination of AM5 at 15 nM and Taxol at 5 nM decrease the number and the size of mammosphere with an improved efficacy than AM5 alone at 15 nM or 5 nM.
Figure 3:
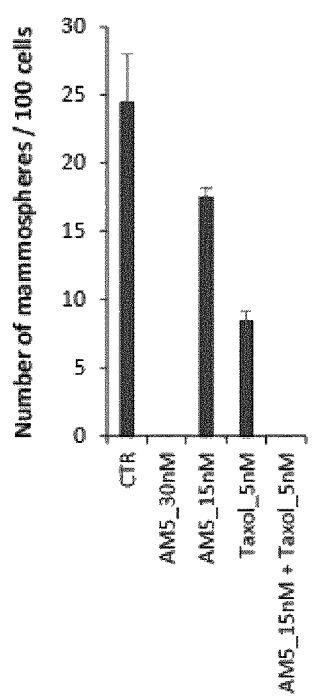
Figure 3:
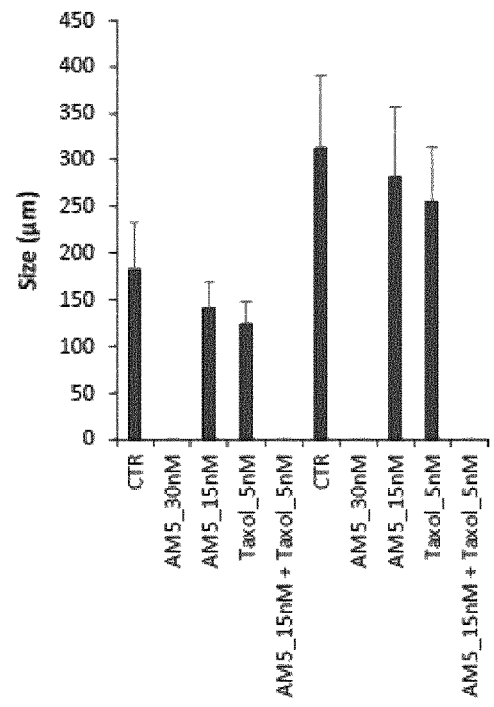

The results are presented in FIG. 3.

The combination of AM5 at 15 nM and Taxol at 5 nM inhibits cell proliferation and mammosphere formation with an improved efficacy than AM5 alone at 15 nM or 5 nM.

Example 5: Effect of AM5 on Xenograft Tumor Formation

Human breast cancer cell line MCF-7 cells cultures were collected, enzymatically dissociated, washed in PBS, and resuspended in PBS/Matrigel mixture (1:1 volume). 0.1 ml of this mixture was then implanted in the mammary fat pad of 5-week-old female AthymicNude-Fox1nu mice (Harlan, France). The mice were maintained in individually-ventilated cages (Tecniplast, France) under constant temperature and humidity; all experiments were performed under laminar flow (Tecniplast France). The mice received estradiol supplementation (0.4 mg/kg) in the same day and 7th day from cell injection, and were observed and palpated for tumor appearance. The mice received Salinomycine analogue (here AM5, 3 mg per kg body weight per day, intra peritoneal injection) every 5 opened days of the week for 33 days. Tumor growth was measured weekly using calipers. Tumor volume was determined using the standard formula: L×W2×0.52, where L and W are the longest and shortest diameters, respectively. All animal work was done according to the Guidelines of the United Kingdom Coordinating Committee on Cancer Research.

The results are presented in FIG. 4.

Following AM5 treatment, the tumor volume and tumor weight were lower.

These results are consistent with the in vitro assay and indicate that the compounds of formula (I) according to the present invention are capable of inhibiting the tumor formation in nude mice.

Example 6: Salinomycin and Active Analogues Trigger Cell Death Through Lysosomal Fenton Catalysis Salinomycine analogue-induced cell death is inhibited by the ROS scavenger N-acetylcysteine (NAC). Cell lines were incubated with or without 500 nM of Sal analogues for 48 h. Apoptosis was evaluated by AnnexinV-FITC and PI staining, and FACS analysis.

The results are presented in FIG. 5. All data are expressed as means±s.d. from three individual experiments (*; P<0.05)

Data indicate that Salinomycine and AM5 induce cell death through lysosomal ROS production.

Example 7: Lysosomal Iron Mediates Salinomycine Analogues-Activated Cell Death Signaling Salinomycine analogue-induced cell death is inhibited by lysosomal iron chelator deferoxamine mesylate (DFO). Cells were treated as in Example 6 with or without the indicated concentration of DFO for 48 h. Apoptosis was evaluated as in Example 6.

The results are presented in FIG. 6.

Data indicate that lysosomal iron mediated Salinomycine analogues activated cell death signaling.

Example 8: Effect of AM5 and AM23 on the Proliferation of HMLER CD24– Cells

AM5 and AM23 and salinomycine were assessed for their capability to inhibit cell proliferation and formation of mammospheres.

The results are presented in FIGS. 7 to 9.

At 30 nM, AM 5 and AM23 inhibit cell proliferation with a ten-fold improved efficacy in comparison with salinomycine.

These results thus indicate that the compounds of formula (I) according to the present invention are capable of inhibiting the formation of mammospheres more efficiently than salinomycine.

Example 9: IC50 of Salinomycin, of AM5 and of AM23 on Breast Cell Lines

Table 1 below represents the IC50 of Salinomycin (Sal) and its derivatives AM5 and AM23 for a wide range of the breast cell lines.

The cells were seeded in a 6-well plate at density 5.105 cells/well and cultured overnight. The cells were then treated with various concentration (15, 30, 100, 500, 1000 and 10.000 nM) of salinomycine, AM5 and AM23 for 72 h, 96 h and 108 h. After treatment, cell death was quantified using Annexin V-FITC/Propidium Iodide (PI) assay according to the manufacturer's protocol (FITC Annexin V Apoptosis Detection Kit II, 556570, BD Pharmingen™) and analyzed by a LSRFortessa™ flow cytometer (BD Bioscience, San Jose, Calif.). The data were processed using Cell Quest software (BD Biosciences). Dose-response cell death curves were determined for indicated time.

For tumor cells, the cells are classified in function of their sensitivity of drugs. Here, the most sensitive cells are incubated for 72 h, the middle sensitive cells for 96 h and the less sensitive or resistant cells are incubated for 108 h with drug at several concentrations.

Concentrations of 30 nM, 500 nm and 1 µM were used for determining the IC50 of drugs.

Intervals]130-500 nM] mean that IC50 is included in this interval with exclusion of the valor 30 nM.

TABLE 1

| Tumor cells | | Sal | AM5 | AM23 |
|---|---|---|---|---|
| No tumoral | HBL100 | >1 µM | >1 µM | >1 µM |
| Immortalized | HMLE W2 | >1 µM | >1 µM | 1 µM |
| 1rst sensibility | HMLER ID2 | >1 µM | >1 µM | <30 nM |
| (72 h) | HMLER CD24low | [30-500] nM | <30 nM | <30 nM |
| | HMLER GFP | 1 µM | 1 µM | 30 nM |
| | HMLER shECAD | [30-500] nM | [30-500] nM | 30 nM |
| | MCF-7 | [30-500] nM | [30-500] nM | ]30-500] nM |
| | Zr75.1 | 500 nM | [30-500] nM | ]30-500] nM |
| 2nd sensibility | MDA-MB-361 | 500 nM | 500 nM | 1 µM |
| (96 h) | MDA-MB-134 | [30-500] nM | [30-500] nM | >1 µM |
| | MDA-MD-157 | 1 µM | 500 nM | [30-500] nM |
| | MDA-MB-231 | >1 µM | >1 µM | >1 µM |
| | BT474 | >1 µM | >1 µM | >1 µM |
| 3rd sensibility | Hs528T | ND | ND | ND |
| (108 h) | BT20 | 500 nM | [30-500] nM | [30-500] nM |
| | SW620 | [500 nM-1 µM] | [30-500] nM | [30-500] nM |
| | SW480 | [30-500] nM | [30-500] nM | [30-500] nM |
| Resistant | BT549 | >1 µM | >1 µM | >1 µM |
| (108 h) | T47D | >1 µM | >1 µM | >1 µM |

The SW620 and SW480 cell lines are from colon tumors. Table 2 describes the essential specificities of each cell line:

TABLE 2

| Name | Essential specificities |
|---|---|
| HBL100 | Human mammary epithelial cell line obtained from primary cultures of cells derived from an early lactation sample of human milk (from ATCC). |
| HMLE W2 | Human mammary epithelial cell line infected with a retrovirus carrying hTERT, SV40 (R. A. Weinberg, Whitehead Institute, Massachusetts Institute of Technology, USA) |
| HMLER ID2 | Human mammary epithelial cell line infected with a retrovirus carrying hTERT, SV40 and the oncogenic allele HrasV12 (R. A. Weinberg, Whitehead Institute, Massachusetts Institute of Technology, USA) |
| HMLER CD24low | HMLER CD44high/CD24low not expressing E-cadherin and expressing Vimentin (was obtained from A. Puisieux INSERM) |
| HMLER shGFP (ctrl) | HMLER cells expressing a control shRNA (shCtrl). Generated by infection with retrovirus encoding the pWZL-GFP plasmid. (R. A. Weinberg, Whitehead Institute, Massachusetts Institute of Technology, USA) |
| HMLER shECAD | transformed HMLER breast cancer cells displaying a short hairpin RNA (shRNA)-mediated inhibition of the human CDH1 gene, which encodes E-cadherin. Generated by infection with retrovirus encoding the pWZL-GFP plasmid. (R. A. Weinberg, Whitehead Institute, Massachusetts Institute of Technology, USA) |
| MCF-7 | Human ductal breast epithelial tumor cell line classified in Estrogen/Progesteron Receptor (ER/PR) positive group and luminal A (from ATCC). |
| Zr75.1 | Human ductal breast epithelial tumor cell line, classified in Estrogen/Progesteron Receptor (ER/PR) and HER-2 positive group and luminal A (from ATCC). |
| MDA-MB-361 | Human ductal breast epithelial tumor cell line, classified in Progesteron Receptor (PR) and HER-2 positive group and luminal B (from ATCC). These cells were isolated from a metastatic site in the brain. |
| MDA-MB-134 | Human ductal breast epithelial tumor cell line classified in Estrogen/Progesteron Receptor (ER/PR) positive group and luminal B (from ATCC). |
| MDA-MD-157 | Human ductal breast epithelial tumor cell line, classified in Estrogen/Progesteron Receptor (ER/PR) and HER-2 negative group and Basal (from ATCC). |

TABLE 2-continued

| Name | Essential specificities |
|---|---|
| MDA-MB-231 | Human ductal breast epithelial tumor cell line, classified in Estrogen/Progesteron Receptor (ER/PR) and HER-2 negative group and Basal (from ATCC). |
| BT474 | Human ductal breast epithelial tumor cell line, classified in Progesteron Receptor (PR) and HER-2 positive group and luminal B (from ATCC). |
| Hs578T | Human ductal breast epithelial tumor cell line, classified in Estrogen/Progesteron Receptor (ER/PR) and HER-2 negative group and Basal (from ATCC). |
| BT20 | Human ductal breast epithelial tumor cell line, classified in Estrogen/Progesteron Receptor (ER/PR) and HER-2 negative group and Basal (from ATCC). |
| SW620 | colon tumor cells; derived from metastatic site: lymph node (from ATCC). |
| SW480 | colon tumor cells; derived from a primary adenocarcinoma of the colon (from ATCC). |
| BT549 | Human ductal breast epithelial tumor cell line, classified in Estrogen/Progesteron Receptor (ER/PR) and HER-2 negative group and Basal (from ATCC). |
| T47D | Human ductal breast epithelial tumor cell line classified in Estrogen/Progesteron Receptor (ER/PR) positive group and luminal A (from ATCC). |

These results indicate that AM5 and AM23 have a IC50 compared to Salinomycin similar or better depending on the cells.

Example 10: Influence of AM23 in ROS Inducement

Reactive Oxygen Species (ROS) levels were measured by flow cytometry or by confocal scanning immunofluorescence microscopy using CM-H2DCF-DA (C6827, invitrogen). Briefly, U2OS and HMLER CD24low cells were treated as indicated in FIG. 11 (30 nM, 500 nM or 1 µM of salinomycine, AM5 or AM23 or untreated during 48 h). Then, these cells were trypsined and incubated with 5 µM CM-H2DCF-DA at 37° C. for 40 min, washed once with PBS and were counterstained with DAPI (0.5 µg/ml) to exclude non-viable cells. The mean fluorescence intensity was determined as ROS production by flow cytometry with LSRFortessa™ cytometer (BD Bioscience, San Jose, Calif.). For immunofluorescence microscopy analysis, cells were seeded on coverslips and were treated with salinomycine derivatives (injection in culture medium then treatment during 24 h, 48 h and 72 h). LysoTracker® Red DND-99 (L-7528, Life technologies) was used to visualize lysosomes. Then, cells were fixed with 4% PFA/PBS. DAPI was used to visualize nuclear DNA. Cell images were obtained using a Deltavision real-time microscope (Applied Precision) or an ApoTome.2 microscope (Zeiss). ImageJ was used for further image processing. As shown in FIG. 11, AM23 induces ROS in HMLER CD24low cells.

Example 11: Intracellular Sodium Measurement and Tumor Growth in MCF-7 Xenograft-Bearing Mice Intracellular sodium measurement: Sodium and potassium buffers (10 mM HEPES, 1 mM CaCl$_2$, 1 mM MgCl$_2$, 130 mM Sodium-D-Gluconate or Potassium-D-Gluconate, 30 mM NaCl/KCl) were mixed at different ratios to produce five buffers with various sodium concentrations (0, 20, 40, 80, 160 mM). Nigericin (N7143, Sigma, 10 µM) and monensin (M5273, Sigma, 10 µM) were used to equilibrate the intracellular sodium concentration and establish a calibration curve. HMLER CD24low cells were harvested and re-suspended in ECS buffer (15 mM HEPES, 5.4 mM KCl, 140 mM NaCl, 10 mM Glucose, 1 mM MgCl$_2$, 1.8 mM CaCl$_2$, 0.1% BSA, pH 7.6) containing 10 µM of the sodiumspecific probe (SBFI-AM, S-1263, Molecular Probes®) and 0.2% Pluronic F-127 (P2443, Sigma) and were incubated for 1 h in the dark at 37° C. Then, cells were washed to remove excess dye and incubated for an additional 30 min in ECS buffer. Cells were introduced into a 96-well plate (1000 cells/well) and treated with salinomycine derivatives in a concentration ranging from 0.03 to 20 µm (AM5: 0.120 µM; AM13: 0.120 µM; AM9: 20 µM; salinomycine: 20 µM and 1 µM) during 5 min. Each well was sequentially excited at 340 and 370 nm and emission was recorded at 500 nm. The spectral response of SBFI upon sodium binding was assessed by excitation ratio measurement (340/370 nm). Measurements were performed on a Perkin Elmer Wallac 1420 Victor2 Microplate Reader at 37° C.

Xenograft tumor formation experiments: MCF-7 cell cultures were collected, enzymatically dissociated, washed with PBS, and re-suspended in a PBS/Matrigel mixture (1:1 v/v). The mixture (0.1 mL) was then implanted in the mammary fat pad of 5-week-old female AthymicNude-Fox1nu mice bilaterally (Harlan, France). Mice were maintained in individually-ventilated cages (Tecniplast, France) under constant temperature and humidity. All experiments were performed under laminar flow (Tecniplast France). Mice received estradiol supplementation (0.4 mg/kg) the same day and 7 days from cell injection, and were observed and palpated for tumor appearance. Mice were treated with AM5 or Paclitaxel (3 mg/kg body weight/day) by means of intraperitoneal injections every 5 opened days of the week. Tumor growth was measured weekly using calipers. Tumor volume was determined using the standard formula: L×W2× 0.52, where L and W are the longest and shortest diameters, respectively. All animal studies were approved by the Direction des services Vétérinaires, Préfecture de Police, Paris, France (authorization number A75-14-08) and the ethical committee (number 34) of Paris Descartes University. No randomization was used and experimenters were blinded to drug treatments and tissue analyses.

While salinomycine induced a fast increase in intracellular sodium using a dose as high as twenty times the IC50 value, salinomycine derivatives had no effect on sodium transport at doses effective against the proliferation of HMLER CD24low cells (FIG. 12). This data challenged the idea that salinomycine selectively affects the maintenance of CSCs by directly altering membrane potentials. In contrast, AM9 was ineffective in these assays validating the carboxylate as a required motif to alter CSC maintenance, and paclitaxel alone was poorly effective against tumorsphere formation.

Moreover, AM5 prevented tumor growth in MCF-7 xenograft-bearing mice (FIG. 13).

Example 12: Toxicity Assessment

Histology. Organs from mice were removed at time of sacrifice. For morphological analyses, organs were fixed with 4% paraformaldehyde, paraffin embedded, and 4-μm sections were stained with hematoxylin and eosin (H&E). Sections were scanned at high resolution using a slide scanner (NanoZoomer 2.0-HT, Hamamatsu, Massy, France). Representative images are shown in FIG. 14.

No generic toxicity was observed upon treatment with an effective dose of AM5 as observed from the integrity of peripheral tissues and a constant body weight throughout treatment (FIG. 15).

All the samples of the lung from both untreated and treated groups showed minimal to moderate multifocal macrophages aggregates in the alveoli. This finding is poorly significant and commonly observed in mice. In 4 mice (2 untreated, 2 treated), extra-pulmonary, interstitial mononuclear cells infiltrates were observed. Most likely poorly significant, not treatment related.

In untreated mouse, a focal sub-pleural pulmonary densification was noticed with interstitial fibrosis and atypical cell infiltrates evoking tumor cells (metastasis). A large artefact on the lesion (tissue fold) interfered with the analysis No significant changes were observed on kidney.

Example 13

MDA-MB-231 cells were cultivated with or without cathepsine B inhibitor (COA74-Me, 30 μM), and/or salinomycine, AM5, or AM23 (500 nM) at indicated duration (48 h, 96 h, 108 h). From the treatment, dead cells were assessed by DIOC6(3)/DAPI test and analyzed by flow cytometry. Graphic representation of percent of dead cells (DIOC6(3) negative/DAPI positive or negative) is shown in FIG. 16. Cathepsine B inhibition and salinomycine, AM5 or AM23 treatment combine themselves to induce the death of human breast cancer cell line MDA-MB-231.

FACS analysis of ROS in cells treated for 48 h is represented in FIG. 17. Pharmacological inhibition of Cathepsin B prevents AM5 from inducing ROS production in HMLER CD24low cells.

The invention claimed is:

1. A compound of formula (I), enantiomers, mixture of enantiomers, diastereoisomers and mixture of diastereoisomers thereof:

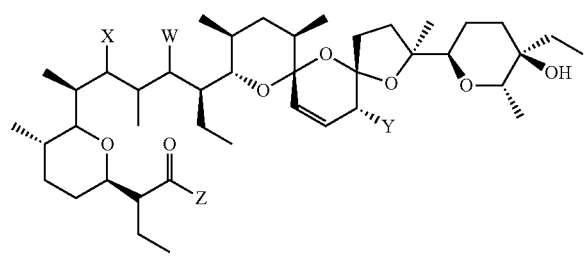

wherein:
W is selected from the group consisting of =O; $-NR_1R_2$; $-NR_3-(CH_2)_n-NR_4R_5$; $-O-(CH_2)_n-NR_4R_5$; $-NR_3-(CH_2)_n-N^+R_6R_7R_8$ and $-O-(CH_2)_n-N^+R_6R_7R_8$;

X is selected from the group consisting of =O, —OH; $-NR_1R_2$; $-NR_3-(CH_2)_n-NR_4R_5$; $-O-(CH_2)_n-NR_4R_5$; $-NR_3-(CH_2)_n-N^+R_6R_7R_8$ and $-O-(CH_2)_n-N^+R_6R_7R_8$, Y is selected from the group consisting of —OH; =N—OH; $-NR_1R_2$; $-NR_3-(CH_2)_n-NR_4R_5$; $-O-(CH_2)_n-NR_4R_5$; $-NR_3-(CH_2)_n-N^+R_6R_7R_8$ and $-O-(CH_2)_n-N^+R_6R_7R_8$, $R_1$ and $R_2$, identical or different, are selected from the group consisting of H; $(C_1-C_{16})$-alkyl; $(C_3-C_{16})$-alkenyl; $(C_3-C_{16})$-alkynyl; $(C_3-C_{16})$-cycloalkyl; aryl; heteroaryl; $(C_1-C_6)$-alkyl-aryl; $(C_1-C_6)$-alkyl-heteroaryl; or $R_1$ represents H and $R_2$ represents $OR_9$, where $R_9$ is H, $(C_1-C_6)$-alkyl, aryl and $(C_1-C_6)$-alkyl-aryl;

$R_3$ is selected from the group consisting of H; $(C_1-C_6)$-alkyl; $(C_1-C_6)$-alkyl-aryl;

$R_4$ and $R_5$, identical or different, are selected from the group consisting of H; $(C_1-C_6)$-alkyl; aryl and $(C_1-C_6)$-alkyl-aryl;

$R_6$, $R_7$ and $R_8$, identical or different, are selected from the group consisting of $(C_1-C_6)$-alkyl; aryl and $(C_1-C_6)$-alkyl-aryl;

Z is selected from the group consisting of OH; $NHNR_9R_{10}$; $NHOC(O)R_{11}$; $N(OH)-C(O)R_{11}$; OOH, $SR_{12}$; 2-aminopyridine; 3-aminopyridine; $-NR_3-(CH_2)_n-NR_4R_5$; and $-NR_3-(CH_2)_n-OH$; where:

$R_9$ and $R_{10}$, identical or different, are selected from the group consisting of H, $(C_1-C_6)$-alkyl, aryl and $(C_1-C_6)$-alkyl-aryl;

$R_{11}$ is selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl;

$R_{12}$ is selected from the group consisting of H; $(C_1-C_{16})$-alkyl; $(C_3-C_{16})$-alkenyl; $(C_3-C_{16})$-alkynyl; aryl; heteroaryl; $(C_1-C_6)$-alkyl-aryl; $(C_1-C_6)$-alkyl-heteroaryl n=0, 2, 3, 4, 5 or 6, with the proviso that at least one of W, X and Y is selected from the group consisting of $-NR_1R_2$; $-NR_3-(CH_2)_n-NR_4R_5$; $-O-(CH_2)_n-NR_4R_5$; $-NR_3-(CH_2)_n-N^+R_6R_7R_8$ and $-O-(CH_2)_n-N^+R_6R_7R_8$.

2. The compound according to claim 1, wherein:
$R_1$ and $R_2$, identical or different, are selected from the group consisting of H; $(C_1-C_{16})$-alkyl; $(C_3-C_{16})$-alkenyl; $(C_3-C_{16})$-alkynyl; $(C_3-C_{16})$-cycloalkyl; and $(C_1-C_6)$-alkyl-heteroaryl, $R_3$ is selected from the group consisting of H; and $(C_1-C_6)$-alkyl;

$R_4$ and $R_5$, identical or different, are selected from the group consisting of H; $(C_1-C_6)$-alkyl; and $(C_1-C_6)$-alkyl-aryl.

3. The compound according to claim 1 or 2, wherein $R_1$ is H and $R_2$ is selected from the group consisting of $(C_1-C_{16})$-alkyl, $-(C_3-C_{16})$-alkenyl, $(C_3-C_{16})$-alkynyl, $(C_3-C_{16})$-cycloalkyl, and $(C_1-C_6)$-alkyl-heteroaryl.

4. The compound of formula (I) according to claim 1, wherein Z is OH or NHOH.

5. The compound according to claim 1, wherein W, X and Y, identical or different, are selected from the group consisting of $-NR_1R_2$; $-NR_3-(CH_2)_n-NR_4R_5$; $-O-$ $(CH_2)_n$—$NR_4R_5$; —$NR_3$—$(CH_2)_n$—$N^+R_6R_7R_8$; and —O—$(CH_2)_n$—$N^+R_6R_7R_8$; $R_1$ to $R_8$ and n being as previously defined.

6. The compound according to claim 1, wherein two of X, Y or Z, identical or different, are selected from the group consisting of —$NR_1R_2$; —$NR_3$—$(CH_2)_n$—$NR_4R_5$; —O—$(CH_2)_n$—$NR_4R_5$; —$NR_1$—$(CH_2)_n$—$N^+R_6R_7R_8$; and —O—$(CH_2)_n$—$N^+R_6R_7R_8$; $R_1$ to $R_8$ and n being as previously defined.

7. The compound of formula (I) according to claim 1, wherein one of X, Y or Z is selected from the group consisting of —$NR_1R_2$; —$NR_3$—$(CH_2)_n$—$NR_4R_5$; —O—$(CH_2)_n$—$NR_4R_5$; —$NR_1$—$(CH_2)_n$—$N^+R_6R_7R_8$; and —O—$(CH_2)_n$—$N^+R_6R_7R_8$; $R_1$ to $R_8$ and n being as previously defined.

8. The compound of formula (I) according to claim 7, wherein X is selected from the group consisting of —$NR_1R_2$, —$NR_3$—$(CH_2)_n$—$NR_4R_5$; —O—$(CH_2)_n$—$NR_4R_5$; —$NR_1$—$(CH_2)_n$—$N^+R_6R_7R_8$; and —O—$(CH_2)_n$—$N^+R_6R_7R_8$ and Y is OH; $R_1$ to $R_8$ and n being as previously defined.

9. The compound of formula (I) according to claim 7, wherein X is selected from the group consisting of =O and OH and Y is selected from the group consisting of —$NR_1R_2$; —$NR_3$—$(CH_2)_n$—$NR_4R_5$; —O—$(CH_2)_n$—$NR_4R_5$; —$NR_1$—$(CH_2)_n$—$N^+R_6R_7R_8$; and —O—$(CH_2)_n$—$N^+R_6R_7R_8$; $R_1$ to $R_8$ and n being as previously defined.

10. The compound according to claim 9, wherein X is OH, Z is OH and Y is $NR_1R_2$ where $R_1$ is H and $R_2$ is selected from the group consisting of ($C_1$-$C_{16}$)-alkyl, ($C_3$-$C_{16}$)-alkenyl, ($C_3$-$C_{16}$)-alkynyl, and ($C_3$-$C_{16}$)-cycloalkyl.

11. The compound according to claim 1, selected from the group consisting of:

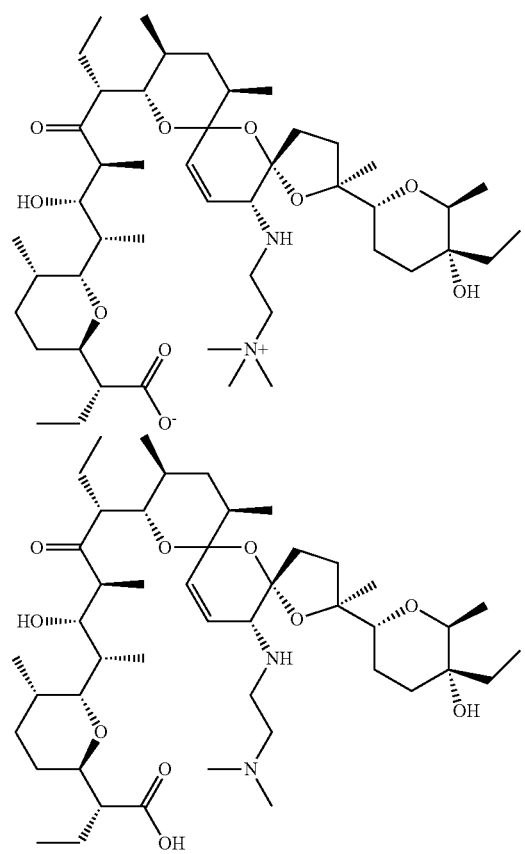

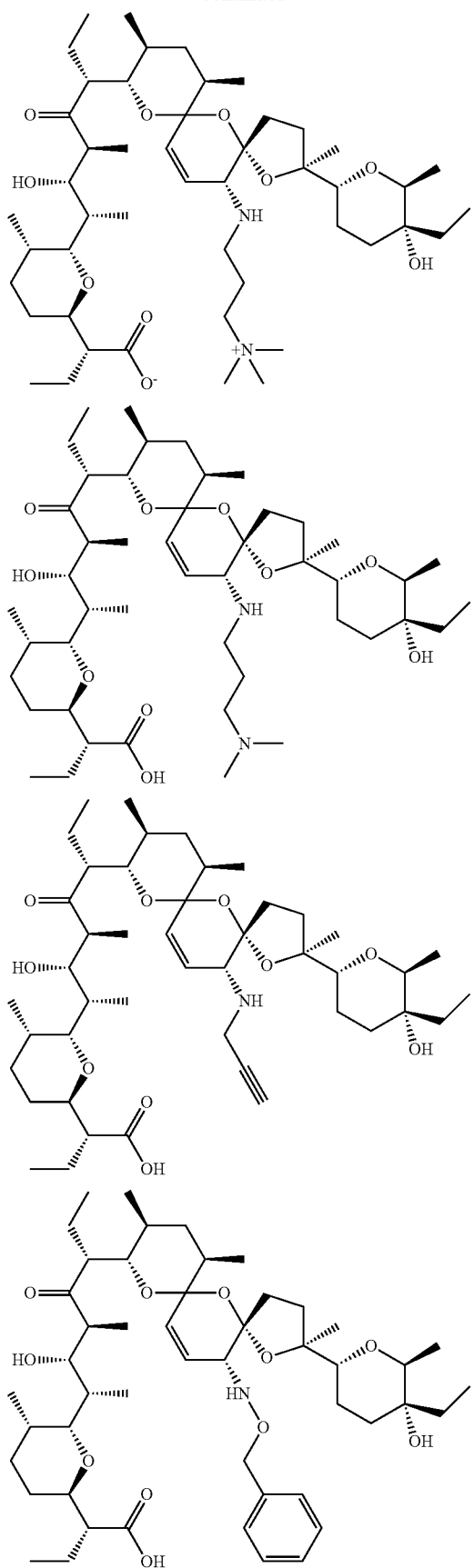

49
-continued
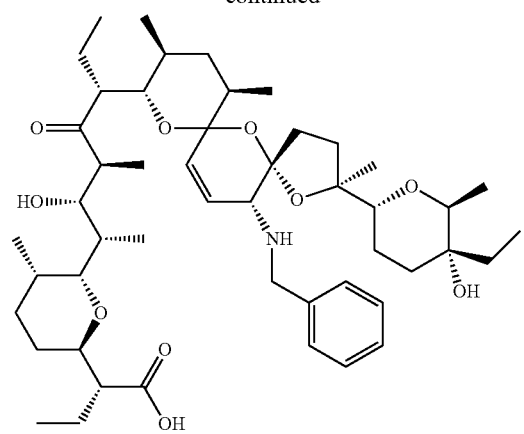
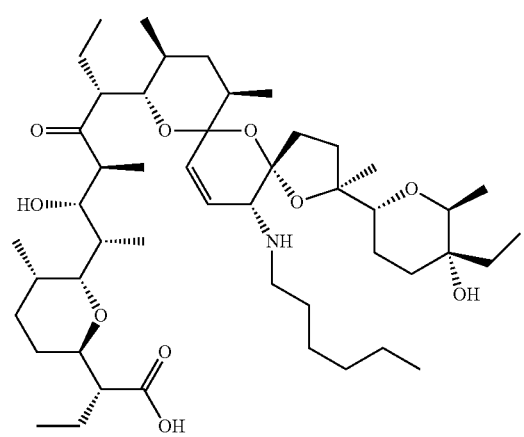
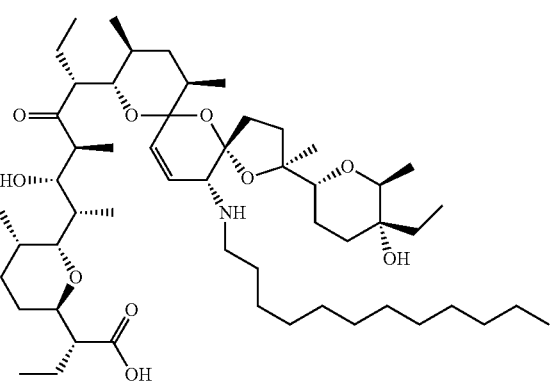
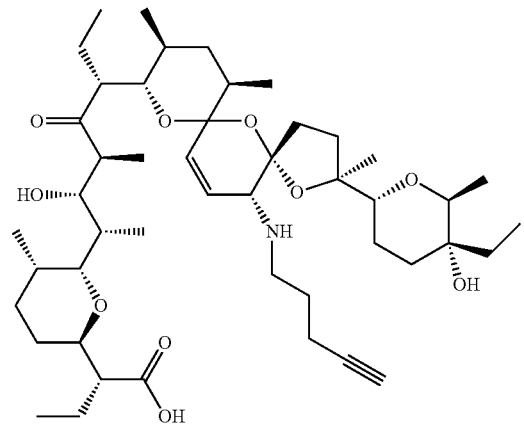
50
-continued
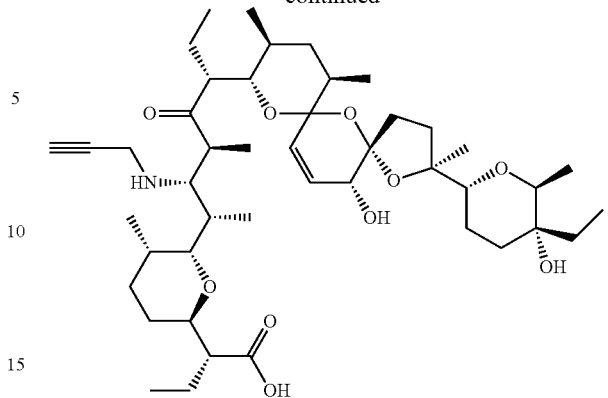
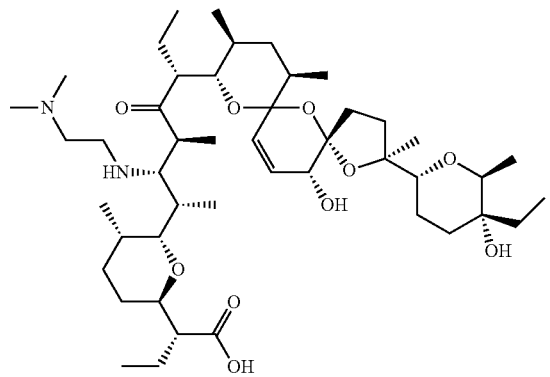
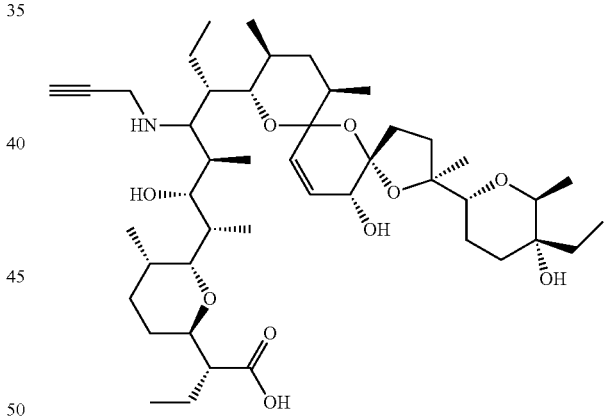
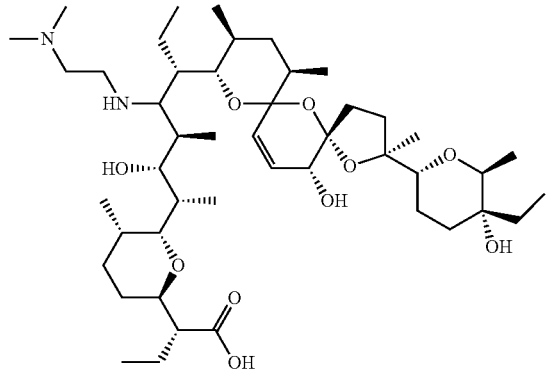

51
-continued
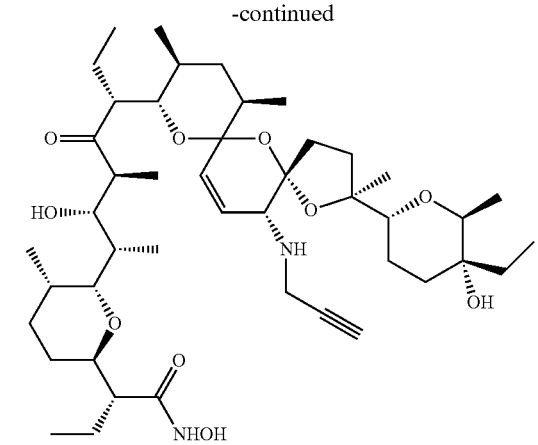
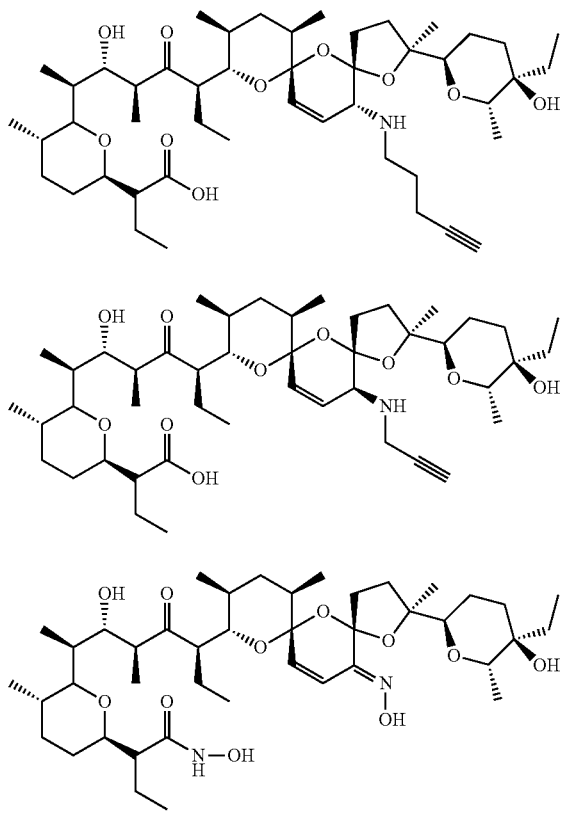
52
-continued
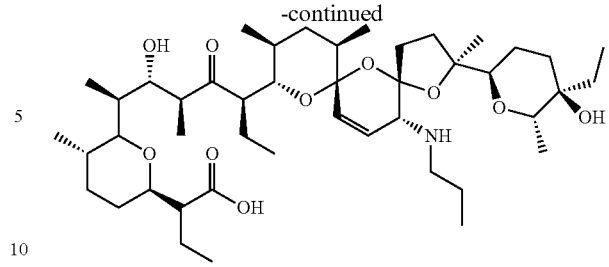
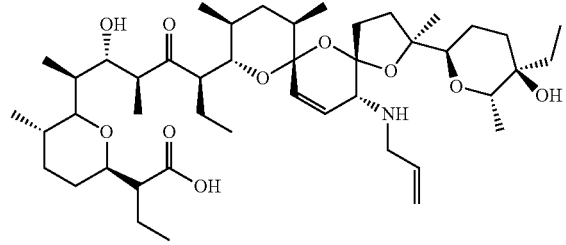
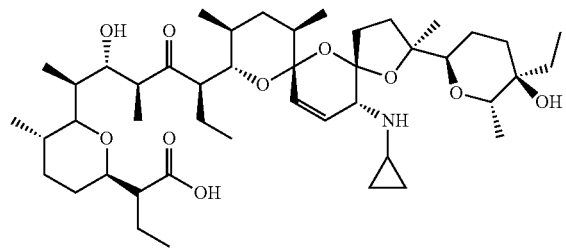
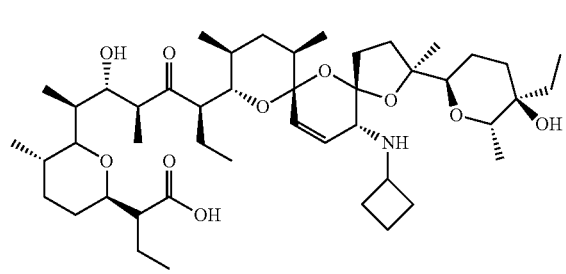
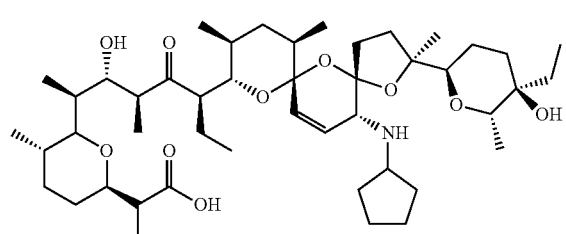
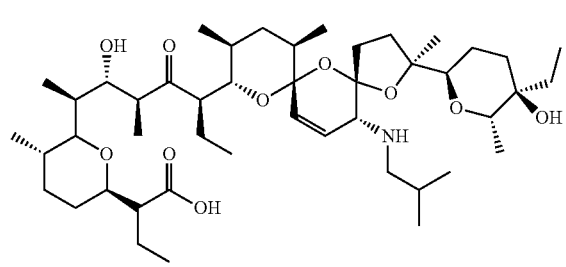
and -continued

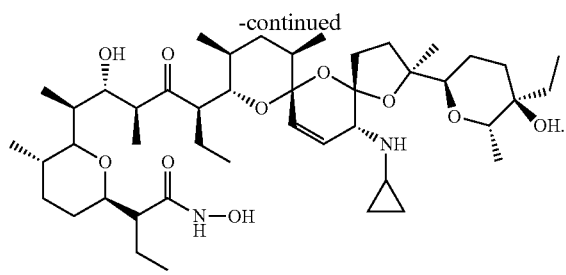

12. The compound according to claim 1 or 2, wherein $R_1$ is H and $R_2$ is selected from the group consisting of $(C_3-C_{14})$-alkyl; $(C_3-C_5)$-alkenyl; $(C_3-C_5)$-alkynyl; $(C_3-C_6)$-cycloalkyl; and $CH_2$-pyridinyl.

13. The compound of formula (I) according to claim 1, wherein Z is OH.

14. The compound of formula (I) according to claim 7, wherein X is selected from the group consisting of —$NR_1R_2$; —$NR_3$—$(CH_2)_n$—$NR_4R_5$ and —O—$(CH_2)_n$—$NR_4R_5$ and Y is OH; $R_1$ to $R_8$ and n being as previously defined.

15. The compound of formula (I) according to claim 7, wherein X is OH and Y is selected from the group consisting of —$NR_1R_2$, —$NR_3$—$(CH_2)_n$—$NR_4R_5$, and —O—$(CH_2)_n$—$NR_4R_5$; $R_1$ to $R_8$ and n being as previously defined.

16. The compound according to claim 9, wherein X is OH, Z is OH and Y is $NR_1R_2$ where $R_1$ is H and $R_2$ is selected from the group consisting of $(C_8-C_{14})$-alkyl, $(C_3-C_5)$-alkenyl, $(C_3-C_5)$-alkynyl, and $(C_3-C_6)$-cycloalkyl.

17. A drug containing the compound according to claim 1.

18. A pharmaceutical composition comprising at least a compound of formula (I) according to claim 1, a pharmaceutically acceptable salt, solvate, or hydrate thereof, and at least one pharmaceutically acceptable excipient.

19. The pharmaceutical composition according to claim 18, further comprising another anticancer drug.

20. The pharmaceutical composition according to claim 19, wherein said other anticancer drug is Adriamycin and Cyclophosphamide or Docetaxel.

21. A combination medicament comprising:
  a) the compound of formula (I) according to claim 1, and
  b) another chemotherapy compound,
for simultaneous, separate, or staggered use.

22. The medicament according to claim 21, wherein said another chemotherapy compound is Adriamycin, Cyclophosphamide, or Docetaxel, and wherein said medicament is used in the treatment of cancer.

23. A method for the treatment of cancer in a subject in need thereof, comprising administering to the subject an effective amount of at least one compound according to claim 1.

24. The method according to claim 23 for reducing the risk of cancer relapse and/or metastases.

25. The method according to claim 23 for the treatment of malaria.

26. The method according to claim 23 for the treatment of breast cancer.

27. A method for the treatment of cancer in a subject in need thereof, comprising administering to the subject an effective amount of at least one pharmaceutical composition according to claim 18.

28. The method according to claim 27 for the treatment of breast cancer.

* * * * *